United States Patent [19]

Blunt et al.

[11] Patent Number: 4,868,204

[45] Date of Patent: Sep. 19, 1989

[54] MYCALAMIDE COMPOUNDS, COMPOSITIONS THEREOF AND METHODS OF PREPARATION AND USE

[75] Inventors: John W. Blunt; Murray H. G. Munro; Nigel B. Perry; Andrew M. Thompson, all of Christchurch, New Zealand

[73] Assignee: Harbor Branch Oceanographic Institution, Inc., Ft. Pierce, Fla.

[21] Appl. No.: 198,199

[22] Filed: May 25, 1988

Related U.S. Application Data

[63] Continuation-in-part of Ser. No. 43,700, Apr. 29, 1987, abandoned.

[51] Int. Cl.$^4$ .............. A61K 31/335; C07D 319/10
[52] U.S. Cl. .................... 514/452; 549/364; 549/332
[58] Field of Search ................. 514/452; 549/364, 332

[56] References Cited

PUBLICATIONS

Capon et al., Tetrahedron, vol. 41, pp. 3391-3404, (1985).

Kato et al., Tetrahedron Letters, vol. 26, pp. 3483-3486, (1985).

*Primary Examiner*—Nicky Chan
*Attorney, Agent, or Firm*—Carroll F. Palmer

[57] ABSTRACT

Mycalamide compounds are derived from marine sponges of the genus Mycale or prepared by synthetic methods. These compounds and pharmaceutical compositions containing them as active ingredients are useful as antitumor and antiviral agents.

22 Claims, No Drawings

MYCALAMIDE COMPOUNDS, COMPOSITIONS THEREOF AND METHODS OF PREPARATION AND USE

REFERENCE TO RELATED APPLICATION

This application is a continuation-in-part of copending application U.S. Ser. No. 043,700, filed Apr. 29, 1987, now abandoned. The disclosure of that application is incorporated herein by reference.

FIELD OF THE INVENTION

This invention relates to new organic compounds, novel biologically active compositions containing one or more of such compounds and methods for the production of such compounds and compositions. More particularly, the invention concerns novel compounds that possess antitumor, antiviral and other biologically active properties and their methods of production and use.

BACKGROUND OF THE INVENTION

Various tumor related diseases inflict man and other mammals and, as these conditions are often fatal, the prevention, control of growth and regression of tumors in mammals has been receiving widespread attention by the medical profession and pharmaceutical industry. The term tumor refers to abnormal masses of new tissue growth which is discordant with the economy of the tissue of origin or the host's body as a whole.

Tumors inflict mammals and man with a variety of disorders and conditions including various forms of cancer and resultant cancerous cachexia, which term refers to the symptomatic discomfort that accompanies the infliction of a mammal with a tumor. Such symptoms include weakened condition of the inflicted mammal as evidenced by weight loss, etc. The seriousness of cancer is well known since cancer is a major cause of death in man.

Considerable research and resources have been devoted to oncology and antitumor measures including chemotherapy. While various antitumor agents and methods have been developed which aid in inhibiting tumors, additional methods and chemical agents are needed.

Viral diseases also inflict man, plants, insects and animals. The prevention and control of viral diseases has important health and economic implications.

Viral diseases contribute to inflictions in humans including common colds, herpes, acquired immune deficiency syndrome and cancer so the importance of their control is obvious. Also important is the control of viral diseases in animals for economic and other reasons, e.g., the ability of such animals to become virus reservovirs or carriers which facilitate the spreading of viral diseases to humans. Viral plant diseases have been known to have a disruptive effect on the cultivation of fruit trees, tobacco and various vegetables. Insect viral diseases are also of interest because of the insects' ability to transfer viral diseases to humans.

The prevention and control of viral diseases is thus of prime importance to man and considerable research has been devoted to antiviral measures. Certain methods and chemical compositions have been developed which aid in inhibiting, controlling or destroying viruses, but additional methods and antiviral compositions are needed.

A potential source for biologically active compounds of great diversity is marine plants and animals. In fact, marine sponges have proved to be a productive source for such compounds. Some such molecules derived from sponges are described in Scheuer, P. J., *Marine Natural Products, Chemical and Biological Perspectives;* Academic Press; New York, 1978-1983; Vol. I-V; Kato et al., Tetrahedron Letters, Vol. 26, Pg. 3483-6 (1985); and Capon and Macleod, Tetrahedron, Vol. 41, Pg. 3391-3404 (1985). The entire disclosures of these references are hereby incorporated herein by reference.

Another naturally derived composition of interest is pederin. Pederin is isolated from insects of the Paederus genus. Pederin shows antimitotic activity as described in British Pat. Nos. 1,078,049 (1967) and 932,875 (1963).

It has now been found that certain compounds derived from extracts of marine sponge of the genus Mycale, family Mycalidae, and order Poecilosclerida, possess useful biological activity.

SUMMARY OF THE INVENTION

The invention provides new compounds having unique biological activities, that have been given the class name mycalamides, compositions containing such compounds and methods for the preparation and for the use of the compounds and the compositions.

The full scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description The objects of the invention are accomplished, in part, by the discovery of novel biologically active compounds of the general formula (I):

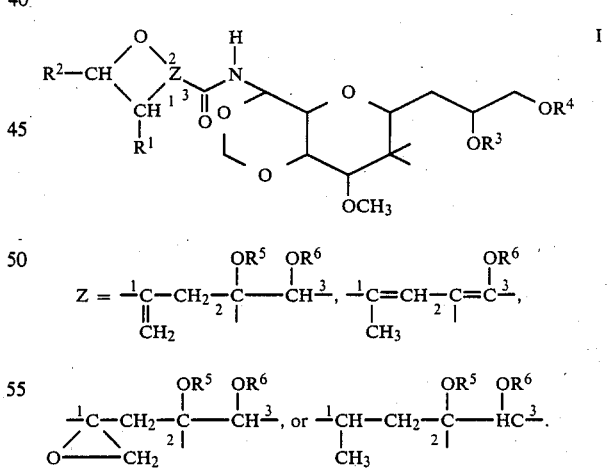

$R^1$ and $R^2$ are the same or different and are hydrogen or lower alkyl, and $R^{3-6}$ are the same or different and are hydrogen, lower alkyl, carboxylic acyl or lower tri-(lower alkyl) silyl.

In preferred embodiments of the invention, the new compounds are in substantially pure form.

In preferred embodiments of the invention $R^1$ and $R^2$ are methyl groups, $R^4$ is hydrogen and Z is:

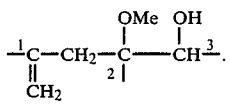

Also provided by discoveries of the invention are pharmaceutical compositions containing between about 0.01 to 50%/w of one of the new compounds of the invention or a mixture of two or more of such compounds and one or more non-toxic, compatible ingredient, e.g., carrier, diluent and/or adjuvant.

A preferred class of the new mycalamide compounds of the invention are those having the formula:

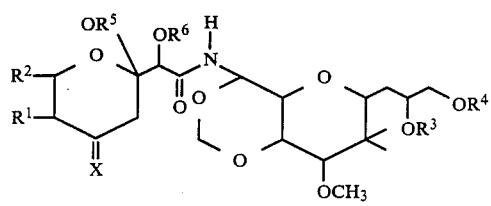

wherein
R$^1$ and R$^2$ are the same or different and are hydrogen or lower alkyl, particularly C1–C5 alkyl,
R$^{3-6}$ are the same or different and are hydrogen, lower alkyl, acyl or lower alkyl silyl, and
X is =CH$_2$,

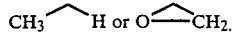

The invention provides a variety of processes for the production of compounds of the invention. A preferred method of producing the new compounds comprises the steps of collecting marine sponge of the genus Mycale, family Mycalidae, and order Poecilosclerida, contacting such sponge with a selected organic solvent system to obtain an extract, fractionating the extract and isolating mycalamide compounds of formula I from the fractionated extract.

In further preferred methods of the invention, some of the new mycalamide compounds are made by hydrogenation in the presence of a hydrogenation catalyst. Also, ion-exchange, hydrolysis, alkylation, acetylation and other known synthesis type reactions may be used pursuant to known procedures to add or modify various groups in preferred compounds to produce other compounds according to the formula I.

As a result of the discoveries by the invention of the new compounds, skilled chemists will be able to use known procedures to synthesize these compounds from available stock substances.

The objects are further accomplished according to the invention by the discovery that viruses and tumors can be inhibited by contact with an effective amount of the new compounds.

DESCRIPTION OF THE PREFERRED EMBODIMENTS

A more complete understanding of the invention can be obtained by reference to preferred embodiments of the invention which are illustrated by the following specific examples of compounds, compositions and methods of the invention. It will be apparent to those skilled in the art that the examples involve use of materials and reagents that are commercially available from known sources, e.g., chemical supply houses, so no details are given respecting them.

The following examples are not intended to be limiting of the scope of the invention, but to provide further understanding of the invention including methods for production of the mycalamide compounds, pharmaceutical compositions containing them and methods of using the compounds and compositions.

EXAMPLE 1

Preparation of Mycalamide A

The compound of the formula:

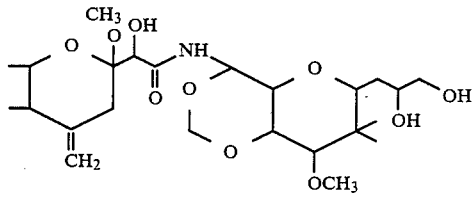

A New Zealand maring sponge of the genus Mycale (family Mycalidae, order Poecilosclerida), was collected from the channel at Aquarium Point, Otago Harbour, New Zealand. 200 gms. of frozen sponge were extracted by blending with 3:1 methanol:toluene and filtering off the solid. On removing the solvents, the combined extracts from three such steps yielded a brown gum (11.04 gms) with antiviral properties. Reverse phase flash chromatography (Blunt et al., J. Nat. Prod. 50, Pg290 (1987) gave bioactive fractions on eluting with 1:1, 3:1 and 9:1 mixtures of H$_2$O:methanol. These were combined to give a brown oil (307 mg). A subsample of this material (140 mg) was applied to a column of Fractogel PGM 2000 (120 gms Fractogel, column 43 cm×2 cm). Eluting with 1:4, H$_2$O:methanol (0.5 ml/min) gave bioactive fractions at around 1.5 void volumes, which were combined (brown oil, 50 mg). Silica gel column chromatography (DAVISIL, 35–60u, 5 gms) starting with CH$_2$Cl$_2$, then increasing amount of methanol, gave 1.7 mg of mycalamide A in the most bioactive fraction, eluted with 1:9 methanol:CH$_2$Cl$_2$.

Spectral data: [α] 365 nm+110° (c 0.2 gm/100 ml, CHCL$_3$)

MS (EI): M+, measured 50.27220 daltons, calculated for C$_{24}$H$_{41}$NO$_{10}$ 503.27305 (−1.7 ppm). M+-methanol, measured 471.24824 daltons, calculated for C$_{23}$H$_{37}$NO$_9$ 471.24683 (+3.0 ppm).

IR, film, (CM−1): 3700–3700, 2690, 1740, 1700, 1540, 1470, 1390, 1100, 1080, 1040.

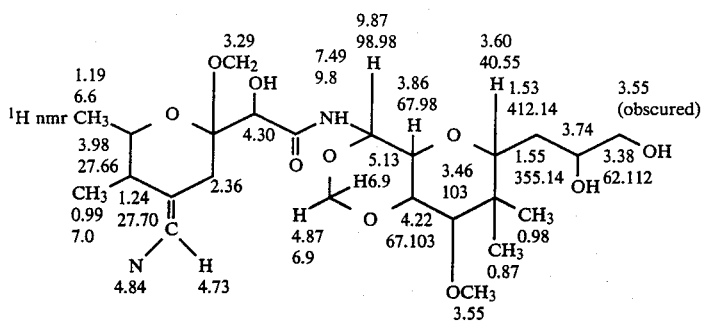

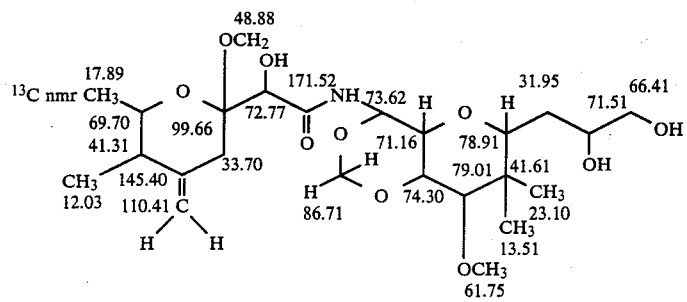

EXAMPLE 2

Preparation of Mycalamide B

The compound of the formula:

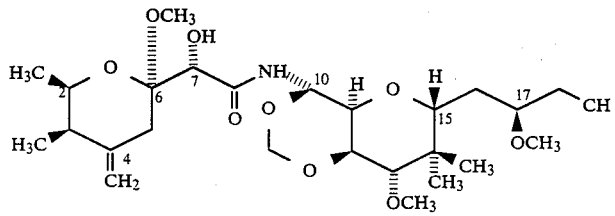

Mycalamide B, an oil having a molecular formula $C_{25}H_{43}NO_{10}$ and a molecular weight of 517, was extracted, using the same general procedure as described in Example 1, from the same sponge, i.e., Mycale sp. (type specimen PML1-9, Chemistry Department, University of Canterbury), family Mycalidae, order Poecilosclerida (Perry, et al. JACS, in press). Experience indicates that mycalamide A & B co-occur in all samples of the active Mycale sp. of sponge.

Spectral data: $(\alpha)_D$ +39° (c 0.2, CHCl$_3$).

HREIMS, M+—CH$_3$O 486.26993 (−0.8 ppm), M+—CH$_3$OH 485.26422 (+3.5 ppm).

DCIMS (NH$_3$) 535 (7%, M+NH$_4$+), 505(28%), 504(38%), 503 (100% M+NH$_4$+—CH$_3$OH), 488(23%), 487(36%), 486(89%).

DCIMS (ND$_3$) 543(5%), 542(14%), 541(10%), 513(17%), 493(8%), 492(9%), 491(15%), 490(36%), 489(37%), 488(16%).

DCIMS (CH$_4$) 488(16%), 487(32%), 486(100%,MH+—CH$_3$OH), 456(16%).

IR(film) 3700–3100, 2950, 1700, 1540, 1470, 1390, 1100, 1080, 1040, 750cm$^{-1}$.

IR(CHCl$_3$) 3600–3300, 2900, 1690, 1390, 1100, 1040cm$^{-1}$.

$^1$H NMR (CDCl$_3$) 7.54(NH9,d,10.0), 5.79(H10,t,9.7), 5.12(10—O—CH$_2$,d,7.0), 4.85(10—O—CH$_2$,d,6.9), 4.85(4=CH$_2$,t,2.0), 4.72(4=CH$_2$,t,1.9), 4.29(H7,s), 4.21(H12,dd,6.7,10.4), 4.02(H2,dq,2.8,6.6), 3.79 (H11,dd,6.7,9.7), 3.65(H18,dd,3.3,11.9), 3.55(13—O—CH$_3$,s), 3.47(H18,dd,5.7,11.9), 3.44(H13,d,10.5), 3.41 (H15,dd,3.2,9.1), 3.29(6—O—CH$_3$,s), 3.24(17—O—CH$_3$,s), 3.2(H17,m), 2.36(H5(eq),d,13.9), 2.22(H5(ax),td,2.0,13.9), 2.24(H3,dq,2,4,6.9), 1.5(H$_2$16,m). 1.20(2—CH$_3$,d,6.6), 1.01(3—CH$_3$,d,7.1), 0.97(14—CH$_3$(eq),s), 0.85(14—CH$_3$(ax),s) ppm(couplings in HZ).

C NMR (CDCL$_3$) 171.88(C8), 145.10(C4), 111.02(4=CH$_2$), 99.95(C6), 86.49(10—O—CH$_2$), 79.27(C13), 78.84(C17), 75.46(C15), 74.44(C12), 73.90(C10), 71.73(C7), 70.94(C11), 69.64(C2), 63.48(C18), 61.78(13—O—CH$_3$) 56.64(17—O—CH$_3$), 48.57(6—O—CH$_3$), 41.47(C14), 41.27(C3), 33.64(C5), 29.63(C16), 23.13(14—CH$_3$(eq)), 17.93(2—CH$_3$), 13.32(14—CH$_3$(ax)), 12.13(3—CH$_3$).

AV assay: 4+, 4+, +*, C7 @2 ng/disk; —; —; — @0.5 ng/disk P388 IC$_{50}$: 0.26 ng/ml.

EXAMPLE 3

Preparation of Mycalamide A 4 γ-epoxide (major product)

The compound of the formula:

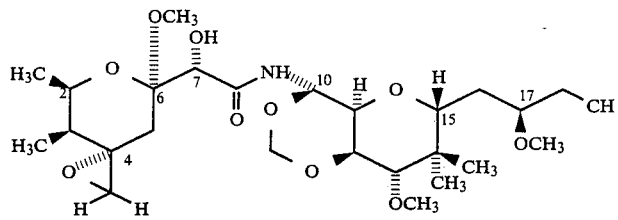

Mycalamide A (2.9 mg) and m-chloroperbenzoic acid (2 mg) were stirred in chloroform for 6 hours. The solvent was removed and the combined organic extract subjected to silica gel chromatography (200 mg Davisil, 150 A, 35–70 um), developed in steps from 50% hexane in ethyl acetate to 10 % ethanol in ethyl acetate. Three fractions (2.3 mg combined) eluting between 5% and 10% ethanol in ethyl acetate contained mycalamide A epoxide, a 2:1 mix of two isomers. These were separated by prep tlc (silica gel 60 $F_{254}$, 0.2 mm) developed twice with 10% ethanol in ethyl acetate. The two bands of silica were recovered and each eluted with 1:1 EtOH:EtOAc giving two extracts (1.0 mg, 0.6 mg) which were epimers of pure mycalamide A epoxide, an oil having a molecular formula $C_{24}H_{41}NO_{11}$ and a molecular weight of 519.

Spectral data:

DCIMS ($NH_3$) 537 (10%, $M+NH_4^+$), 505(22% $M+NH_4^+$—$CH_3OH$), 488(17%,$MH^+$—$CH_3OH$), 487(15%), 335(34%), 262(16%), 231(24%), 230(34%).

$^1H$ NMR ($CDCl_3$) 7.40(NH9,d,9.7), 5.88(H10,t,9.8), 5.14(10—O—$CH_2$, d,7.0), 4.88(10—O—$CH_2$,d,7.0), 4.34(H2,dq,2.4,6.6), 4.31(H7,s), 4.24(H12,dd,6.8,10.4), 3.86(H11,dd,6.8,10.0), 3.74(H17,m), 3.61(H15,dd,4.1,5.2) 3.56(H18,m,hidden), 3.56(13—O—$CH_3$,s), 3.38(H18,dd,5.8,11.3), 3.37(6—O—$CH_3$,s), 3.47(H13,d,10.4), 2.55(4—$CH_2O$,d,4.5), 2.52(4—$CH_2O$,d,4.5), 2.22(HS(ax,d,14.8), 1.55($H_2$16,m), 1.43(HS(eq),dd,1.3,14.8), 1.21(2—$CH_3$,d,6.6), 1.12(H3,m), 1.00(3—$CH_3$,d,7.1), 0.98(14—$CH_3$(eq),s), 0.88)14—$CH_3$(ax),s) ppm(couplings in Hz).

C NMR ($CDCl_3$) 99.63(C6), 86.88(10—O—$CH_2$), 79.20(C13), 79.00(C15), 74.47(C12), 73.62(C10), 73.28(C7), 71.65(C17), 71.42(C11), 67.18(C2), 66.57(C18), 61.86(13—O—$CH_3$), 58.39(C4), 50.68(4—$CH_2O$), 49.05(6—O—$CH_3$), 41.74(C14), 39.71(C3), 31.93(C16), 31.40(C5), 23.05(14—$CH_3$(eq)), 17.53(2—$CH_3$), 13.37(14—$CH_3$(ax)), 9.75(3—$CH_3$).

AV assay: 3+, 4+, +*, @200ng/disk; ++; +; +* @50 ng/disk.

P388 $IC_{50}$: 34 ng/ml.

EXAMPLE 4

Preparation of Mycalamide A 4β-epoxide (minor product)

The compound of the formula:

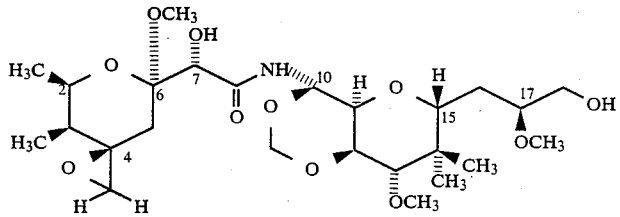

Mycalamide A (2.9 mg) and m-chloroperbenzoic acid (2 mg) were stirred in chloroform for 6 hours. The solvent was removed and the combined organic extract subjected to silica gel chromatography (200 mg Davisil, 150 A, 35–70 um), developed in steps from 50% hexane in ethyl acetate to 10% ethanol in ethyl acetate. Three fractions (2.3 mg combined) eluting between 5% and 10% ethanol in ethyl acetate contained mycalamide A epoxide, a 2:1 mix of two isomers. These were separated by prep tlc (silica gel 60 $F_{254}$, 0.2 mm) developed twice with 10% ethanol in ethyl acetate. The two bands of silica were recovered and each eluted with 1:1 EtOH:EtOAc giving two extracts (1.0 mg, 0.6 mg) which were epimers of pure mycalamide A epoxide, an oil having a molecular formula $C_{24}H_{41}NO_{11}$ and a molecular weight of 519.

Spectral data:

DCIMS ($NH_3$) 537 (24%,$M+NH_4^+$), 505(23% $M+NH_4^+$—$CH_3OH$), 488(15%,$MH^+$—$CH_3OH$), 292(22%), 291(34%), 278(23%), 264(31%).

$^1H$ NMR ($CDCl_3$) 7.33(NH9,d,9.9), 5.88(H10,t,9.8), 5.14(10—O—$CH_2$,d,7.0), 4.88(10—O—$CH_2$,d,7.0), 4.32(H7,2), 4.24(H12,dd,6.6,10.5), 4.15(H2,dq,2.5,6.6), 3.86(H11,dd,6.7,10.0), 3.73(H17,m), 3.63(H14,dd,4.0,5.6) 3.56(13—O—$CH_3$,s), 3.55(H18,m,hidden), 3.47(H13,d,10.3), 3.39(H18,dd,6.6,11.0), 3.32(6—O—$CH_3$,s), 2.79(4—$CH_2O$,d,4.9), 2.71(4—$CH_2O$,dd,1.6,4.8), 2.10(HS(ax),dd,1.7,13.4), 1.55($H_2$16,m), 1.43(HS(eq),dd,1.1,13.6), 1.25(H3,m) 1.23(2—$CH_3$,d,6.6), 1.02(3—$CH_3$,d,7.0), 0.98(14—$CH_3$(eq),s), 0.88(14—$CH_3$(ax),s) ppm(couplings in Hz).

$^{13}C$ NMR ($CDCl_3$) 100.49(C6), 86.83(10—O—$CH_2$), 79.11(C13), 78.77(C15), 74.46(C12), 73.77(C10), 72.58(C7), 71.19(C17), 71.29(C11), 68.80(C2), 66.46(C18), 61.87(13—O—$CH_3$), 58.62(C4), 56.92(4—$CH_2O$), 48.60(6—O—$CH_3$), 41.71(C14), 39.97(C3), 32.23(C16,C5), 23.09(14—$CH_3$(eq), 17.74(2—$CH_3$) 13.41(14—$CH_3$(ax)), 7.95(3—$CH_3$).

AV assay: 4+, 3+, +*, @ 50 ng/disk; 2+; +; +* @ 20 ng/disk.

P388 IC$_{50}$: 14.9 ng/ml CB.

EXAMPLE 5

Preparation of Mycalamide B 4 α-epoxide (major product)

The compound of the formula:

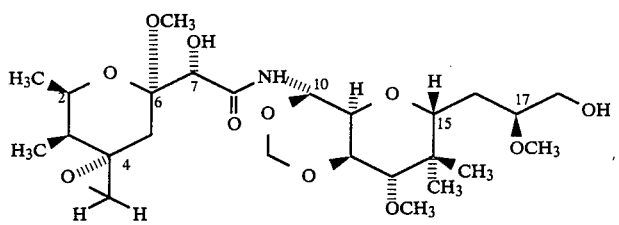

Mycalamide B (6.8 mg) and m-chloroperbenzoic acid (6.5 mg) were stirred in chloroform for 2.5 days. The the combined organic extract was then transferred directly onto a prep tlc plate (silica gel 60 F$_{254}$, 0.2 mm) and developed twice with 5% ethanol in ethyl acetate. Visualisation in vanillin/sulfuric acid show two separate brown bands at medium Rf. The silica was recovered and eluted with 1:1 EtOH:EtOAc giving two extracts. The solvent was removed and the two products (4 mg, 1.6 mg) were epimers of pure mycalamide A epoxide, an oil having a molecular formula C$_{25}$H$_{43}$NO$_{11}$ and a molecular weight of 533.

Spectral data:

DCIMS (NH$_3$) 551 (14%, M+NH$_4$+), 519(23% M+NH$_4^{30}$ —CH$_3$OH), 502(36%,MH+—CH$_3$OH), 409(12%), 386(15%), 351(15%), 349(15%), 306(23%), 294(22%), 276(20%), 264(80%).

$^1$H NMR (CDCl$_3$) 7.44(NH9,d,9.2), 5.77(H10,t,9.6), 5.13(10—O—CH$_2$,d,7.0), 4.85(10—O—CH$_2$,d,7.0), 4.35(H2,dq,2.4,6.7), 4.30(H7,s), 4.22(H12,dd,6.7,10.2), 3.82(H11,dd,6.7,9.7), 3.62(H18,dd,3.1,12.0), 3.55(13—O—CH$_3$,s), 3.46(H18,dd,6.4,11.5), 3.44(H13,d,10.2), 3.38(H15,dd,2.7,9.2), 3.37(6—O—CH$_3$,s), 3.30(17—O—CH,s), 3.26(H17,m) 2.53(4—CH$_2$O,d,4.6), 2.51(4—CH$_2$O,d,4.6), 2.13(HS(ax),d,14.8), 1.56(H$_2$16,m), 1.44(HS(eq),dd,1.0,14.8), 1.22(2—CH$_3$,d,6.9), 1.12(H3,m,), 1.01(3—CH$_3$,d,7.2), 0.98(14—CH$_3$(eq),s), 0.87 (14—CH$_3$(ax),s) ppm(couplings in Hz).

$^{13}$C NMR (CDCL$_3$) 171.30(C8), 99.69(C6), 88.60(10—O—CH$_2$), 79.36(C13), 79.24(C17). 75.36(C15), 74.48(C12), 73.77(C10), 72.81(C7), 70.83(C11), 67.18(C2), 63.94(C18), 61.81(13—O—CH$_3$), 58.32(C4), 56.73(17—O—CH$_3$), 50.51(4—CH$_2$O), 48.87(6—OCH$_3$), 41.54(C14), 39.74(C3), 31.38(C5), 29.47(C16), 23.16(14—CH$_3$(eq)), 17.56(2—CH$_3$), 13.38(14—CH$_3$(ax)), 9.82(3—CH$_3$).

EXAMPLE 6

Preparation of Mycalamide B 4δ-epoxide (minor product)

The compound of the formula:

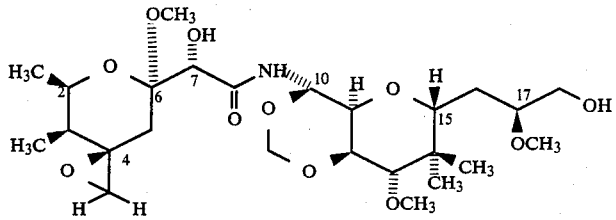

Mycalamide B (6.8 mg) and a m-chloroperbenzoic acid (6.5 mg) were stirred in chloroform for 2.5 days. The the combined organic extract was then transferred directly onto a prep tlc plate (silica gel 60 F$_{254}$, 0.2 mm) and developed twice with 5% ethanol in ethyl acetate. Visualisation in vanillin/sulfuric acid show two separate brown bands at medium Rf. The silica was recovered and eluted with 1:1 EtOH:EtOAc giving two extracts. The solvent was removed and the two products (4 mg, 1.6 mg) were epimers of pure mycalamide A epoxide, an oil having a molecular formula C$_{25}$H$_{43}$NO$_{11}$ and a molecular weight of 533.

Spectral data:

DCIMS (NH$_3$) 551 (17%, M+NH$_4$+), 542(16%), 528(50%), 519(32% M+NH$_4^+$—CH$_3$OH), 503(23%), 502(75%,MH+—CH$_3$OH), 408(16%), 406(16%), 400(27%), 391(18%), 386(58%), 373(22%), 372(100%).

$^1$H NMR (CDCl$_3$) 7.43(NH9,d,9.9), 5.80(H10,t,9.6), 5.13(10—)CH$_2$,d,7.0), 4.86(10—O—CH$_2$,d,6.9), 4.31(H7,s), 4.23(H12,dd,6.8,10.4), 4.18(H2,dq,2.6,6.7), 3.81(H11,dd,6.8,9.7), 3.64(H18,m), 3.56(13—O—CH$_3$,s), 3.44(H18,m,hidden), 3.43(H13,d,10.2), 3.38(H15,M), 3.32(6—O—CH$_3$,s), 3.32(17—O—CH$_3$,s), 3.24(H17,m) 2.78(4—CH-2O,d,4.9), 2.69(4—CH$_2$O,dd,1.5,4.9), 2.03(H5(ax),dd,1.5,13.2), 1.56(H$_2$16,m), 1.42(H5(eq),dd,0.8,13.3), 1.25(H3,m) 1.24(2—CH$_3$, d,6.7), 1.04(3—CH$_3$,d,7.0), 0.99(14—CH$_3$(eq),s), 0.88(14—CH$_3$(ax),s) ppm(couplings in Hz).

$^{13}$C NMR (CDCl$_3$) 100.72(C6), 86.53(10—O—CH$_2$), 79.36(C13), 78.78(C17). 75.60(C15), 74.48(C12), 73.98(C10), 71.62(C7), 68.84(C2), 63.36(C18), 61.82(13—O—CH$_3$), 58.42(C4), 56.76(4—CH$_2$O), 56.59(17—O—CH$_3$),48.37(6—O—CH$_3$), 41.74(C14), 40.09(C3), 32.00(C5), 29.75(C16), 23.22(14—CH$_3$(eq)), 17.80(2—CH$_3$), 8.06(3—CH$_3$). NB. C8, C11 and 14—CH$_3$(ax) not observed.

EXAMPLE 7

Mycalamide A Triacetate

The compound of the formula:

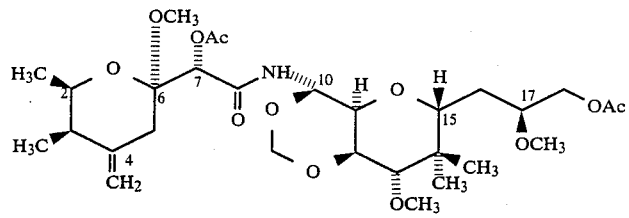

Mycalamide A (2 mg) was dissolved in pyridine (0.5 ml) and acetic anhydride (0.5 ml). After 7 hr. at 21° C., water (1 ml) was added and the mixture extracted with CHCl$_3$ (3×1 ml). The solvent was removed and the combined organic extracts were subjected to silica gel chromotography (200 mg Davisil, 150 A, 35–70 um), developed in steps from hexane to ethyl acetate. A fraction (1.2 mg) eluted with 1:1 hexane:ethyl acetate was pure mycalamide triacetate, an oil of molecular weight 629 and molecular formula C$_{30}$H$_{47}$NO$_{13}$.

Spectral data:
HREIMS M+—CH$_3$O 598.2800(−10.6 ppm), M+—CH$_3$OH 597.27536(−5.3 ppm).
DCIMS (NH$_3$) 647 (13%, M+NH$_4$), 617(29%), 616(37%), 615(100%,M+NH$_4$+—CH$_3$OH), 542(35%), 318(42%), 317(44%), 299(30%), 286(58%), 285(41%), 270(28%), 269(60%), 257(30%).
DCIMS (CH$_4$) 598(71%,MH+—CH$_3$OH), 538(100%,MH+—CH$_3$OH—CH$_3$CO$_2$H), 299(53%), 269(60%), 240(41%), 208(55%).
IR (CHCl$_3$) 3380, 2950, 2870, 1745, 1380, 1100, 1030 cm$^{-1}$
$^1$H NMR (CDCl$_3$) 7.32(NH9,d,9.4), 5.76(H10,t,9.0), 5.47(H7,s), 5.06(10—O—CH$_2$,d,6.9), 4.98(H17,m), 4.87(4=CH$_2$,m), 4.86(10—O—CH$_2$,d,7.0), 4.76(4=CH$_2$,m), 4.27(H18,dd,2.7,12.4), 4.14(H18,dd,5.2,12.4), 4.10(H12,dd,6.0,9.4), 3.99(H2,d1,2.8,6.6), 3.79(H11,dd,6.0,8.7), 3.52(13—O—CH$_3$,s), 3.36(H13,d,9.4), 3.45(H15,dd,2.4,9.8), 3.18(6—O—CH$_3$,s), 2.4(H$_2$5,m), 2.25(H3,dq,2.7,7.0), 2.20(7—O.CO.CH$_3$,s), 2.05 and 2.00(17—O.CO.CH$_3$,s and 18—O.CO.CH$_3$,2xs), 1.7–1.8(H$_2$16,m), 1.20(2—CH$_3$,d,6.6), 1.03(3—CH$_3$,7.1), 1.01(14—CH$_3$(eq),s), 0.86(14—CH$_3$(ax),s) ppm(couplings in Hz).
$^{13}$C NMR (CDCL$_3$) 170.60(C8), 169.85 & 167.64 & 167.01(7—O—CO, 17—O—CO & 18—O—C), 145.08(C4), 110.85(4=CH$_2$), 99.26(C6), 86.53(10—O—CH$_2$), 79.73(C13), 75.53(C15), 74.06(C12), 73.72(C10), 71.66(C7), 70.01(C17), 69.91(C11), 69.73(C2), 63.57(C18), 61.55(13—O—CH$_3$), 48.60(6—O—CH$_3$), 41.24(C14,C3), 34.18(C5), 30.08(C16), 23.69(14—CH$_3$(eq)), 21.06 & 20.80 & 20.65(7—, 17—, & 18—O—COCH$_3$), 17.87(2—CH$_3$), 14.4(14—CH$_3$(ax)), 12.04(3—CH$_3$)ppm.
AV assay: 3+, 3+, +*, @ 1000 ng/disk; −, −, − @ 250 ng/disk.

P388 IC$_{50}$: 51.9 ng/ml.

EXAMPLE 8

Mycalamide A Tripropanoate

The compound of the formula:

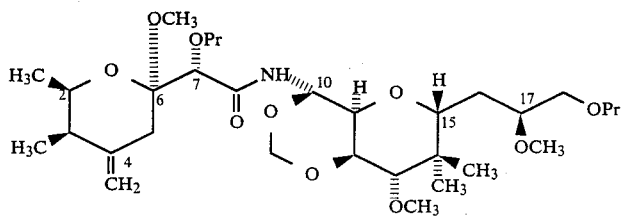

Mycalamide A (2.8 mg) was dissolved in pyridine (0.2 ml) and propionic anhydride (0.1 ml) and stirred overnight at room temperature. Water (0.2 ml) was added and the mixture extracted with CHCl$_3$ (3×0.4 ml). The solvent was removed to give 3.7 mg of pure mycalamide tripropanoate, an oil of molecular weight 671 and molecular formula C$_{33}$H$_{53}$NO$_{13}$.

Spectral data:
DCIMS (NH$_3$) 689(20%, M+NH$_4$), 657(24%,M+NH$_4$+—CH$_3$OH), 404(23%), 346(52%), 331(44%), 314(28%), 244(85%).
$^1$H NMR (CDCl$_3$) 7.34(NH9,d,9.5), 5.77(H10,t,9.0), 5.48(H7,s), 5.06(10—O—CH$_2$,d,7.0), 4.97(H17,m), 4.85(4=CH$_2$,m), 4.85(10—O—CH$_2$,d,6.8), 4.75(4=CH$_2$,t,1.7), 4.28(H18,dd,2.8,12.4), 4.16(H18,dd,5.2,12.4), 4.12(H12,dd,6.0,9.4), 3.99(HZ,d1,2.8,6.6), 3.79(H11,dd,6.1,8.7), 3.52(13—O—CH$_3$,s), 3.45(H15,dd,2.5,9.8), 3.37(H13,d,9.4), 3.17(6—O—CH$_3$,s), 2.49. 2.37 & 2.29 (7—O.CO.CH$_2$, 17—O.CO.CH$_2$&18—O.CO.CH$_2$,m), 2.4(H$_2$5,hidden), 2.3(H3,hidden), 1.77(H16,ddd,2.4,9.3,14.3), 1.6–1.7(16,m), 1.19(2—CH$_3$,d,6.6), 1.0–1.21(7—,17—&18—O.-CO.CH$_2$CH$_3$,m), 1.02(3—CH$_3$,d,7.1), 0.99(14—CH$_3$(eq),s), 0.85(14—CH$_3$(ax),s) ppm(couplings in Hz).
$^{13}$C NMR (CDCL$_3$) 173.95,173.21&173.12(7—,1-7—&18—O—CO), 145.15(C4), 110.77(4=CH$_2$), 99.32(C6), 86.52(10—O—CH$_2$), 79.70(C13), 75.45(C15), 74.03(C12), 73.78(C10), 71.50(C7), 69.96(C17,C11), 69.61(C2), 63.25(C18), 61.56(13—O—CH$_3$), 48.60(6—O—CH$_3$), 41.25(C14,C3), 34.26(C5), 30.10(C16), 27.55, 27.46 & 27.34(7—,17—&1-8—O—COCH$_2$), 23.65(14—CH$_3$(eq)), 17.88(2—CH$_3$), 12.03(3—CH$_3$), 9.11, 9.02 & 8.90(7—,17—&1-8—OCOCH$_2$CH$_3$)ppm. NB. C8, 14—CH$_3$(ax) not observed.
AV assay: 4+, 4+, +*, @ 500 ng/disk; +, −, − @ 200 ng/disk;
P388 IC$_{50}$: 85.6 ng/ml

EXAMPLE 9

Mycalamide B Diacetate

The compound of the formula:

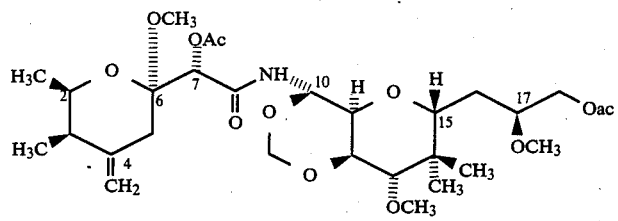

Mycalamide B (3.5 mg) was dissolved in pyridine (0.1 ml) and acetic anhydride (0.1 ml). After 4 hr. at 21° C., water (0.2 ml) was added and the mixture extracted with CHCl$_3$ (3×0.2 ml). The solvent was removed and the combined organic extracts were subjected to silica gel chromatography (200 mg Davisil, 150 A, 35–70 um), developed in steps from hexane to ethyl acetate. A fraction (3 mg) eluted with 1:1 hexane:ethyl acetate was pure mycalamide diacetate, an oil of molecular weight 601 and molecular formula C$_{29}$H$_{47}$NO$_{12}$.

Spectral data:

DCIMS (NH$_3$) 619(22%, M+NH$_4$), 589(16%), 588(32%), 587(100%,M+NH$_4$+—CH$_3$OH), 570(25%,MH+—CH$_3$OH), 318(19%), 290(25%), 258(62%), 257(26%), 241(45%).

IR (CHCL$_3$) 3400, 2950, 2900, 1750, 1710, 1380, 1100, 1030, 910 cm$^{-1}$.

$^1$H NMR (CDCl$_3$) 7.27(NH9,d,9.4), 5.75(H10,t,9.4), 5.45(H7,s), 5.07(10—O—CH$_2$,d,7.0), 4.88(4=CH$_2$,m), 4.85(10—O—CH$_2$,d,6.9), 4.75(4=CH$_2$,m), 4.28(H18,dd,2.5,12.3), 4.17(H12,dd,6.6,10.2), 4.07(H18,dd,4.7,12.5), 4.02(H2,dq,2.8,6.7), 3.77(H11,dd,6.5,9.4), 3.53(13—O—CH$_3$,s), 3.39(H13,d,9.8), 3.3(H17,m), 3.3(H15,hidden), 3.25(17—O—CH$_3$,s), 3.17(6—O—CH$_3$,s), 2.4(H25,m), 2.28(H3,dq,2.7,7.3), 2.20(7—O.CO.C$_3$,s), 2.08(18—O.C.CH$_3$,s), 1.6–1.7(H$_2$16,m), 1.22(2—CH$_3$,d,6.5), 1.04(3—CH$_3$,d,7.2), 0.97(14—CH$_3$(eq),s), 0.86(14—CH$_3$(ax),s) ppm(couplings in Hz).

—C NMR (CDCL$_3$) 170.85(C8), 169.68 & 166.67(7—&18—O—CO), 144.75(C4), 111.26(4=CH$_2$), 99.15(C6), 86.53(10—O—CH$_2$), 79.43(C13), 77.93(C17), 75.68(C15), 74.18(C12), 74.02(C10), 71.48(C7), 70.64(C11), 69.95(C2), 63.48(C18), 61.70(13—O—CH$_3$), 56.88(17—O—CH$_3$), 48.49(6—O—CH$_3$), 41.24(C14), 41.16(C3), 34.39(C5), 30.33(C16), 23.38(14—CH$_3$(eq)), 20.97 & 20.65(7—O—COCH$_3$, & 18—O—COCH$_3$), 17.92(2—CH$_3$), 13.8(14—CH$_3$(ax),broad), 12.19(3—CH$_3$)ppm.

AV assay: 4+, 4+, +*, @ 1000 ng/disk; —, —, — @ 250 ng/disk.

P388 IC$_{50}$: 15.3 ng/ml.

EXAMPLE 10

Mycalamide A 7-mono-p-bromobenzoate.

The compound of the formula:

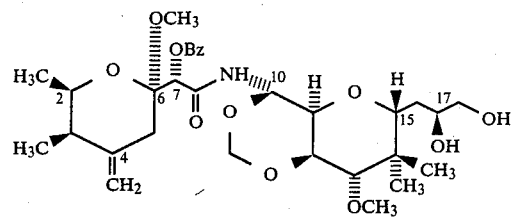

Mycalamide A (2.7 mg), p-bromobenzoyl chloride (5 mg) and triethylamine (2.9 mg) were stirred in CH$_2$CL$_2$ at room temperature for 24 hours. Column chromatography on Davisil (0.2 g) gave a mixture of two products (2 mg ca.) and unreacted mycalamide A (0.8 mg.). Prep RPLC (20% H$_2$O in MeOH) gave two fractions (1.3 mg, 0.5 mg) which were pure mycalamide A mono-p-bromobenzoates at C18—O and C7—O respectively, the latter being a white solid having a molecular weight of 686 and a molecular formula C$_{31}$H$_{44}$BrNO$_{11}$.

Spectral data:

$^1$H NMR (CDCl$_3$) 7.96(7—OCOC$_6$H$_4$Br,d,8.8), 7.62(7—OCOC$_6$H$_4$Br,d,8.7), 7.40(NH9,d,9.5), 5.83(H10, t,9.6), 5.70(H7,s,), 5.10(10—OCH$_2$,d,6.9), 4.90(4=CH$_2$,m), 4.89(10—OCH$_2$,d,7.0), 4.82(4=CH$_2$,m), 4.21(H12,dd,7.1,10.4), 4.05(H2,dq,2.7,6.4), 3.79(H11,dd,6.8,10.0), 3.70(H17,m), 3.60(H15,m), 3.54(13—OCH$_3$,s), 3.47(H18,m), 3.41(H13,d,10.2), 3.29(H18,dd,7.1,11.5), 3.21(6—OCH$_3$,s), 2.64(H5(ax), broad d,14.1), 2.46(H5(eq),d,14.6), 2.30(H3,dq,2.8,6.9), 1.5(H$_2$16,m), 1.24(2—CH$_3$,d,6.5), 1.06(3—CH$_3$,d,7.2), 0.93(14—CH$_3$(eq),s), 0.85(14—CH$_3$(ax),s) ppm(couplings in Hz).

AV assay: 4+, 4+, +*, @ 200 ng/disk, —, +, +* @ 50 ng/ml P388 IC$_{50}$ 23.3 ng/ml.

EXAMPLE 11

Mycalamide A 18-mono-p-bromobenzoate.

The compound of the formula:

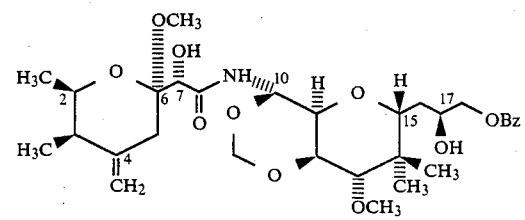

prepared as stated in Example 10 is a white solid having a molecular weight of 686 and a molecular formula C$_{31}$H$_{44}$BrNO$_{11}$.

Spectral data:

$^1$H NMR (CDCl$_3$) 7.89(18—OCOC$_6$H$_4$Br,d,8.6), 7.57(18—OCOC$_6$H$_4$Br,d,8.7), 7.49(NH9,d,10.2), 5.88(H10, t,9.6), 5.14(10—OCH$_2$,d,6.9), 4.88(10—OCH$_2$,d,6.9), 4.83(4=CH$_2$,t,1.6), 4.68(4=CH$_2$,t,1.0), 4.28(H7d,2.6), 4.23(H$_2$18,m), 4.23(H12,dd,6.5,10.5), 4.03(H17,m), 3.98(H2,dq,2.7,6.6), 3.86(H11,dd,6.6,9.8), 3.76(C7—OH,d,2.6), 3.71(H15,dd,2.3,9.9), 3.56(13—OCH$_3$,s), 3.47(H13,d,10.3), 3.27(6—OCH$_3$,s), 3.20(C17—OH,m), 2.4(H$_2$5,m), 2.23(H3,dq,2.6,6.9), 1.5-1.7(H$_2$16,m), 1.18(2—CH$_3$,d,6.6), 1.00(14—CH$_3$(eq),s), 0.98(3—CH$_3$,d,7.0), 0.90(14—CH$_3$(ax),s) ppm(couplings in Hz).

AV assay: 3+, 4+, +*, @ 2 ng/disk; —, —, —, @ 0.5 ng/disk

P388 IC$_{50}$ 1.28 ng/ml.

EXAMPLE 12

Mycalamide A 7,18-di-p-bromobenzoate

The compound of the formula:

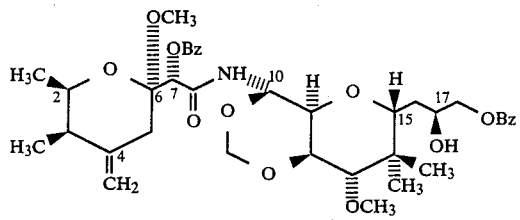

Mycalamide A (11 mg), p-bromobenzoyl chloride (23 mg) and triethylamine (10 mg) were stirred in CH$_2$CL$_2$ at room temperature for 24 hours. Column chromatography on Davisil (0.2 g) gave a mixture of five products (12 mg ca.). Prep RPLC (15% H$_2$O in MeOH) gave five fractions (0.7 mg, 2.7 mg, 1.2 mg, 2.5 mg, 2.7 mg) which were the two mycalamide A mono-p-bromobenzoates at C18—O and C7—O, two isomers of less saturated mycalamide A dibenzoates (named neomycalamide A 7,18-dibenzoate) and mycalamide A 7,18-di-p-bromobenzoate, which is a white solid having a molecular weight of 869 and a molecular formula C$_{38}$H$_{47}$Br$_2$No$_{12}$.

Spectral data:
$^1$H NMR (CDCl$_3$) 7.91 & 7.89(7—&1-8—OCOC$_6$H$_4$Br,d,8.5), 7.56 & 7,51(7—&1-8—OCOC$_6$H$_4$Br,d,8.6), 7.45(NH9,d,9.1), 5.85(H10, t,9.4), 5.7(H7,s), 5.11(10—OCH$_2$,d,6.9), 4.90(10—OCH$_2$,d,6.9), 4.88(4=CH$_2$,t,1.9), 4.72(4=CH$_2$,t,1.8), 4.21(H12,dd,6.3,10.9), 4.2(H$_2$18,m), 4.04(H2,dq,2.7,6.7), 4.03(H17,m), 3.82(H11,dd,6.7,9.7), 3.76(H15,dd,2.7,9.7), 3.55(13—OCH$_3$,s), 3.44(H13,d,10.5), 3.20(6—OCH$_3$,s), 2.69(H5(ax),broad d,14.4), 2.42(H5(eq),d.14.4), 2.30(H3,dq,2.8,7.0), 1.6-1.7(H$_2$16,m), 1.23(2—CH$_3$,d,6.6), 1.05(3—CH$_3$,d,7.0), 0.96(14—CH$_3$(eq),s), 0.88(14—CH$_3$(ax),s) ppm(couplings in Hz).

$^{13}$C NMR (CDCl$_3$) 167.22 & 165.72(7—&1-8—O—CO), 144.67(C4), 131.82, 131.74, 131.50, 131.28, 131.14, 129.04, 128.74 & 128.17(7—&1-8—OCOC$_6$H$_4$Br), 111.24(4=CH$_2$), 99.43(C6), 86.88(10—O—CH$_2$), 79.06(C13), 79.03(C15), 74.54(C12), 74.31(C10), 72.10(C7), 71.58(C11), 70.18(C17), 68.82(C2), 68.45(C18), 61.80(13—O—CH$_3$), 48.61(6—O—CH$_3$), 41.62(C14), 41.23(C3), 34.24(C5), 32.81(C16), 23.20(14—CH$_3$(eq)), 17.89(2—CH$_3$), 13.66(14—CH$_3$(ax)), 12.14(3—CH$_3$)ppm. NB. C8 not observed.

AV assay: 4+, 4+, +*, @ 2000 ng/disk; +, 2+, +* @ 5000 ng/disk

P388 IC$_{50}$: 141.2 ng/ml.

EXAMPLE 13

Neomycalamide A 7,18-di-p-bromobenzoate

The compound of the formula:

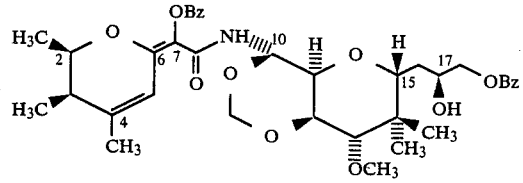

From the preparation of mycalamide A di-p-bromobenzoate in Example 12, two further mycalamide analogs were separated and analysed by PMR. These result from the loss of methanol across C6-C7 and migration of the exocyclic double bond at C4 to C4-C5 position under slightly acidic conditions. The first isomer was unstable and changed overnight in CDCL$_3$ solution into the second, which differs only in the stereochemistry at the new C6-C7 double bond and appears to be a stable white solid of molecular weight 837 and a molecular formula of C$_{37}$H$_{43}$Br$_2$No$_{11}$.

Spectral data:
$^1$H NMR (CDCl$_3$) 8.09(NH9,d,9.0),7.95 & 7.87(7—&18—OCOC$_6$H$_4$Br,d,8.6), 7.56 & 7.50(7—&1-8—OCOC$_6$H$_4$Br,d,8.6), 5.99(H10),t,9.7), 5.97(HS,q,1.5), 5.15(10—OCH$_2$,d,6.8), 4.88(10—OCH$_2$,d,7.0), 4.33(H2,dq,2.8,6.4), 4.26(H$_2$18,m), 4.25(H12,m,hidden), 4.07(H17,m), 3.89(H11,dd,6.7,10.2), 3.67(H15,broad d,9.6), 3.55(13—OCH$_3$,s), 3.48(H13,d,10.6), 2.06(H3,dq,2.8,7.2), 1.83(4—CH$_3$, d,1.5), 1.6-1.7(H$_2$16,m), 1.41(2—CH$_3$,d,6.5), 0.99(3—CH$_3$,d.7.0), 0.95(14—CH$_3$(eq),s), 0.89(14—CH$_3$(ax),s) ppm(couplings in Hz).

AV assay: 4+, 4+, +*, @ 2000 ng/disk; —, —, — @ 500 ng/disk

P388 IC$_{50}$: 572.5 ng/ml.

EXAMPLE 14

Mycalamide A 17,18-bis-trimethylsilylether

The compound of the formula:

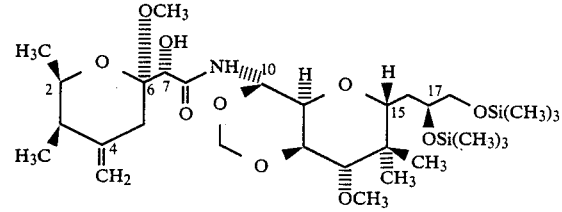

Mycalamide A (1 mg), was dissolved in pyridine (0.1 ml) and cooled in ice. BSA (N,O-bistrimethylsilyl acetamide) (0.1 ml) was added and the reaction was allowed to proceed for four minutes. Water (0.5 ml) was then added and the mixture extracted with CH$_2$Cl$_2$ (30×0.2 ml). The solvent was removed and the combined organic extracts were subject to silica gel chromatography (200 mg Davisil, 150 A, 35-70 um), developed in steps from hexane to ethyl acetate. A fraction (1.3 mg)

eluted with 2:1 hexane:ethyl acetate was pure mycalamide A 17,18-bis-trimethylsilylether by PMR, being an oil having a molecular weight of 647 and a molecular formula $C_{30}H_{57}NO_{10}Si_2$.

Spectral data:

HREIMS M+—CH$_3$O 616.3292 (−7.3 ppm), M+—CH$_3$OH 615.3263 (+0.7 ppm).

$^1$H NMR (CD$_2$Cl$_2$) 7.54(NH9,d,9.6), 5.72(H10),t,9.1), 5.12(10—OCH$_2$,d,7.0), 4.87(4=CH$_2$,t,1.8), 4.83(10—OCH$_2$,d,7.0), 4.71(4=CH$_2$,t,1.8), 4.22(H7,d,2.6), 4.14(H12,dd,6.3,9.5), 3.99(H2,dq,2.8,6.6), 3.94(7—OH,d,2.6), 3.82(H11,dd,6.5,9.0), 3.73(H17,m), 3.53(13—OCH$_3$,s), 3.52(H$_2$18,m), 3.42(H13,d,10.0), 3.35(H15,dd,2.1,10.1), 3.28(6—OCH$_3$,s), 2.34(H5(eq),d,14.0), 2.27(H3,dq,2.3,6.8), 2.24(H5(ax),td,2.2,14.0), 1.71(H16,ddd,2.0,9.7,14.4), 1.45(H16,m) 1.21(2—CH$_3$,d,6.6), 1.02(3—CH$_3$,d,7.3), 1.01(14—CH$_3$(eq),s), 0.86(14—CH$_3$(ax),s), 0.14(18—OSi(CH$_3$)$_3$,s), 0.06(17—OSi(CH$_3$)$_3$,s), ppm(couplings in Hz).

AV assay: 4+, 4+, +*, @ 20 ng/disk; 2+, 3+, +* @ 5 ng/disk

P388 IC$_{50}$: 1.2 ng/ml.

EXAMPLE 15

Mycalamide A tris-trimethylsilylether

The compound of the formula:

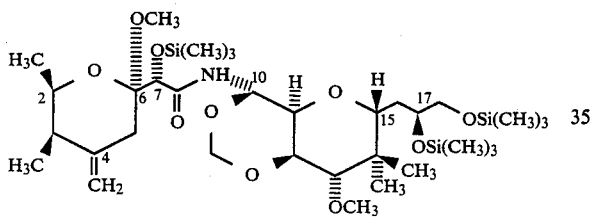

Mycalamide A (2.5 mg), was dissolved in pyridine (0.1 ml) and BSA (N,O-bistrimethylsilyl acetamide) (0.1 ml) was added and the reaction mixture was stirred overnight at room temperature. Water (0.3 ml) was added and the mixture extracted with CH$_2$Cl$_2$ (3×0.2 ml). The solvent was removed and the combined organic extracts were subject to silica gel chromatography (200 mg Davisil, 150 A, 35–70 um), developed in steps from hexane to ethyl acetate. A fraction (3 mg) eluted with 4:1 hexane:ethyl acetate was pure mycalamide A tris-trimethylsilylether, being an oil having a molecular weight of 719 and a molecular formula $C_{33}H_{65}NO_{10}SI_3$.

Spectral data:

HREIMS M+—CH$_3$O 688.3742 (+1.4 ppm), M+—CH$_3$OH 687.3651 (−0.4 ppm).

$^1$H NMR (CDCl$_3$) 7.38(NH9,d,9.6), 5.76(H10,t,9.7), 5.11(10—OCH$_2$,d,6.9), 4.81(10—OCH$_2$,d,6.9), 4.81(4=CH$_2$,t,2.0), 4.71(4=CH$_2$,t,2.1), 4.25(H7,s), 4.17(H12,dd,6.4,10.2), 3.88(H2,dq,2.7,6.6), 3.77(H11,dd,6.4,9.5), 3.72(H17,m), 3.54(13—OCH$_3$,s), 3.53(H18,dd,2.4,12.1), 3.47(H18,dd,4.4,11.4), 3.42(H13,d,10.3), 3.34(H15,dd,1.7,9.9), 3.28(6—OCH$_3$,s), 2.58(H5(eq),d,14.5), 2.35(HS(ax),td,1.9,14.7), 2.19(H3,dq,2.6,6.8), 1.74(H16,ddd,2.0,10.3,13.8), 1.43(H16,m) 1.18(2—CH$_3$,d,6.6), 1.00(3—CH$_3$,d.7.0), 0.98(14—CH$_3$(eq),s), 0.86(14—CH$_3$(ax),s), 0.21(7—OSi(CH$_3$)$_3$,s), 0.10 & 0.06(17—, 18—OSi(CH$_3$)$_3$,s), ppm(couplings in Hz).

$^1$H NMR (CD$_2$Cl$_2$) 7.40(NH9,d,9.8), 5.73(H10,t,9.6), 5.13(10—OCH$_2$,d,7.1), 4.81(10—OCH$_2$,d,7.0), 4.81(4=CH$_2$,t,2.2), 4.68(4=CH$_2$,t,2.0), 4.23(H7,s), 4.15(H12,dd,6.5,9.8), 3.86(H2,dq,2.6,6.6), 3.78(H11,dd,6.4,9.3), 3.73(H17,m), 3.54(13—OCH$_3$,s), 3.53(H18,m), 3.48(H18,dd,4.4,11.8), 3.44(H13,d,10.0), 3.33(H15,dd,1.9,10.1), 3.27(6—OCH$_3$,s), 2.54(HS(eq),d,14.2), 2.35(HS(ax),td,2.1,14.4), 2.21(H3,dq,2.7,7.0), 1.75(H16,ddd,2.0,10.0,14.0), 1.43(H16,m) 1.19(2—CH$_3$,d,6.6), 1.01(3—CH$_3$,d.7.0), 1.01(14—CH$_3$(eq),s), 0.86(14—CH$_3$(ax),s), 0.22(7—OSi(CH$_3$)$_3$,s), 0.12 & 0.07(17—, 18—OSi(CH$_3$)$_3$,s), ppm(couplings in Hz).

$^{13}$C NMR (CD$_2$Cl$_2$) 167.95(C8), 147.37(C4), 109.57(4=CH$_2$), 99.51(C$_6$), 86.48(10—O—CH$_2$), 79.75(C13), 77.70(C15), 76.00(C7), 74.35(C17), 73.37(C10), 70.67(C11, braod), 70.27(C13), 69.66(C2), 65.28(C18), 61.57(13—O—CH$_3$) 50.05(61—O—CH$_3$), 41.59(C3), 41.37(C14), 36.11(C5), 33.36(C16), 23.40(14—CH$_3$(eq)), 17.85(2—CH$_3$), 13.89(14—CH$_3$(ax)), 11.78(3—CH$_3$) and 0.31, 0.27 & −0.39(7—, 17—&18—OSi(CH$_3$)$_3$).

AV assay: 4+, 4+, +*, @ 20 ng/disk; −, −, − @ 5 ng/disk

P388 IC$_{50}$: 1.3 ng/ml.

EXAMPLE 16

Mycalamide A 18-mono-t-butyl,dimethylsilylether

The compound of the formula:

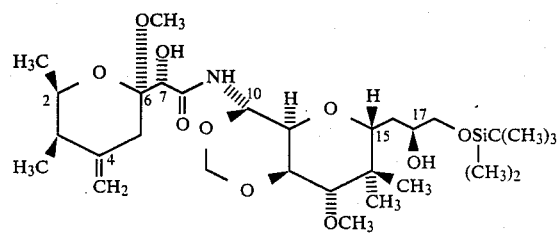

Mycalamide A (1 mg), t-butyldimethylchlorosilane (8 mg), dimethylaminopyridine (1 mg) and trimethylamine (4 mg) were stirred in pyridine (0.2 ml) at room temperature for three hours. Water (0.5 ml) was added and the mixture extracted with CH$_2$Cl$_2$. The organic extract was washed with water (3×0.3 ml), the solvent was removed and the combined product subjected to silica gel chromatography (200 mg Davisil, 150 A, 35–70 um), developed in steps from hexane to ethyl acetate. The major fraction (0.8 mg) eluted with 2:1 hexane:ethyl acetate was pure mycalamide A 18-mono-TBDMS ether, an oil having a molecular weight of 617 and a molecular formula $C_{30}H_{55}NO_{10}Si$.

Spectral data:

$^1$H NMR (CD$_2$Cl$_2$) 7.46(NH9,d,9.7), 5.83(H10,t,9.7), 5.14(10—OCH$_2$,d,7.0), 4.86(10—OCH$_2$,d,-b 7.0), 4.85(4=CH$_2$m), 4.71(4=CH$_2$,m), 4.25(H7,d,2.6), 4.17(H12,dd,6.6,10.2), 3.99(H2,dq,2.8,6.6), 3.84(H11,dd,6.4,9.2), 3.79(7—OH,d,2.6), 3.62(H17,m), 3.54(13—OCH$_3$,s), 3.53(H18,m), 3.5(H15,hidden), 3.47(H18,m), 3.46(H13,d,hidden), 3.28(6—OCH$_3$,s), 2,80(17—OH,d,2.8), 2.30(H5,m), 2.26(H3,dq,2.6,7.1), 1.73(H16,m), 1.5(H16,m) 1.20(2—CH$_3$,d,6.6), 1.01(3—CH$_3$,d.7.1), 1.01(14—CH$_3$(eq),s), 0.90(SiC(CH$_3$)$_3$,s), 0.88(14—CH$_3$(ax),s), 0.08(18—OSi(CH$_3$)$_2$,s) ppm(couplings in Hz).

$^{13}$C NMR (CD$_2$Cl$_2$) 110.19(4=CH$_2$), 99.99(C6), 86.88(10—O—CH$_2$), 79.57(C13), 79.07(C15), 74.40(C12), 74.08(C10), 72.61(C7), 71.37(C17), 69.82(C2), 66.54(C18), 61.66(13—O—CH$_3$) 48.76(6—O—CH$_3$), 41.60(C3), 33.83(C5), 32.36(C16), 25.84(18—OSiC(CH$_3$)$_3$), 23.27(14—CH$_3$(eq)), 17.81(2—CH$_3$), 13.90(14—CH$_3$(ax)), 12.09(3—CH$_3$), −5.48(18—OSi(CH$_3$)$_2$). NB. C4, C8, C11, C14, 18—OSiC not observed.

AV assay: 4+, 4+, +*, @ 20 ng/disk; −, −, − @ 5 ng/disk

P388 IC$_{50}$ 28.5 ng/ml.

EXAMPLE 17

Mycalamide B 18-mono-trimethylsilylether

The compound of the formula:

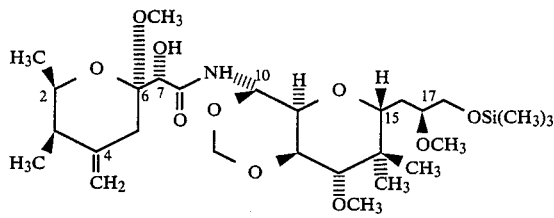

Mycalamide B (0.7 mg) was dissolved in pyridine (0.1 mg) and cooled in ice. BSA (N,O-bistrimethylsilyl acetamide) (0.1 ml) was added and the reaction was allowed to proceed for four minutes. Water (0.5 ml) was then added and the mixture extracted with CH$_2$Cl$_2$ (3×0.2 ml). The solvent was removed and the combined organic extracts were subjected to silica gel chromatography (200 mg Davisil, 150 Å, 35–70 um), developed in steps from hexane to ethyl acetate, A fraction (1 mg) eluted with 4:1 hexane:ethyl acetate was pure mycalamide B 18-mono-trimethylsilylether by PMR, being an oil having a molecular weight of 589 and a molecular formula C$_{28}$H$_{51}$NO$_{10}$Si.

Spectral data:

HREIMS M+—CH$_3$O 558.3048 (−9 ppm), M+—CH$_3$OH 557.3022 (−0.4 ppm).

$^1$H NMR (CDCl$_3$) 7.52(NH9,d,10.1), 5.79(H10,t,9.4), 5.13(10—OCH$_2$,d,6.9), 4.86(4=CH$_2$,m), 4.85(10—OCH$_2$,d,6.9), 4.73(4=CH$_2$,t,1.8), 4.26(H7,broad s), 4.19(H12,dd,6.2,10.0), 4.05(H2,dq,2.9,6.5), 3.98(7—OH,d,2.3), 3.79(H11,dd,6.6,9.3), 3.64(H18,dd,2.6,11.4), 3.55(13—OCH$_3$,s), 3.51(H18,dd,4.2,11.6), 3.41(H13,d,10.5), 3.33(H15,m), 3.31(6—OCH$_3$,s), 3.23(17—OCH$_3$,s), 3.14(H17,m), 2.34(H5(eq),d,13.8), 2.26(H3,dq,2.6,7.1), 2.18(H5(ax),td,2.4,13.9), 1.72(H16,ddd,1.8,9.8,13.8), 1.5–1.6(H16,m) 1.20(2—CH$_3$,d,6.6), 1.02(3—CH$_3$d,7.2), 1.00(14—CH$_3$(eq),s), 0.87(14—CH$_3$(ax),s), 0.13(18—OSi(CH$_3$)$_3$,s), ppm(couplings in Hz).

$^1$H NMR (CD$_2$Cl$_2$) 7.51(NH9,d,9.8), 5.77(H10,t,9.3), 5.13(10—OCH$_2$,d,6.9), 4.86(4=CH$_2$,t,2.0), 4.84(10—OCH$_2$,d,7.0), 4.70(4=CH$_2$,t,1.9), 4.24(H7,d,2.9), 4.16(H12,dd,6.3,9.8), 4.02(H2,dq,2.8,6.6), 3.94(7—OH,d,2.8), 3.80(H11,dd,6.4,9.2), 3.64(H18,dd,2.6,11.5), 3.54(13—OCH$_3$,s), 3.52(H18,dd,4.5,11.5), 3.43(H13,d,10.3), 3.34(H15,dd,2.0,10.1), 3.28(6—OCH$_3$,s), 3.20(16—OCH$_3$,s), 3.14(H17,m), 2.30(H5(eq),d,14.0), 2.27(H3,dq,2.4,6.6), 2.17(H5(ax),td,2.2,14.0), 1.69(H16,ddd,2.0,9.7,14.2), 1.5(H16,m) 1.21(2—CH$_3$,d,6.6), 1.02(3—CH$_3$,d.7.2), 1.01(14—CH$_3$(eq),s), 0.87(14—CH$_3$(ax),s), 0.13(18—OSi(CH$_3$)$_3$,s), ppm(couplings in Hz).

$^{13}$C NMR (CD$_2$Cl$_2$) 171.98(C8), 145.95(C4), 110.69(4=CH$_2$), 100.14(C6), 86.59(10—O—CH$_2$), 79.82(C13), 78.92(C17), 76.25(C15), 74.36(C12), 74.19(C10), 71.71(C7), 70.38(C11), 69.69(C2), 62.17(C18), 61.60(13—O—CH$_3$), 56.69(C17—OCH$_3$), 48.48(6—O—CH$_3$), 41.57(C3), 41.51(C14), 33.75(C5), 29.67(C16), 23.45(14—CH$_3$(eq)), 17.89(2—CH$_3$), 13.93(14 —CH$_3$(ax),s), 12.31(3—CH$_3$), −0.55(18—OSi(CH$_3$)$_3$).

AV assay: 4+, 4+, +*, @ 0.2 ng/disk; −, −, −@ 0.05 ng/disk

P388 IC$_{50}$ 0.08 ng/ml.

EXAMPLE 18

Mycalamide B bis-trimethylsilylether

The compound of the formula:

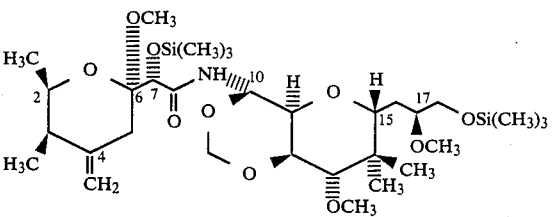

Mycalamide B (2.6 mg) was dissolved in pyridine (0.1 ml) and BSA (N,O-bistrimethylsilyl acetamide) (0.1 ml) and the reaction mixture was stirred overnight at room temperature. Water (0.3 ml) was added and the mixture extracted with CH$_2$Cl$_2$ (3×0.2 ml). The solvent was removed and the combined organic extracts were subject to silica gel chromatography (200 mg Davisil, 150 Å, 35–70 um), developed in steps from hexane to ethyl acetate. A fraction (3.1 mg) eluted with 4:1 hexane:ethyl acetate was pure mycalamide B bistrimethylsilylether, being an oil having a molecular weight of 661 and a molecular formula C$_{31}$H$_{59}$NO$_{10}$Si$_2$.

Spectral data:

HREIMS M+—CH$_3$O 630.3318 (−28 ppm), M+—CH$_3$OH 629.3418 (+0.5 ppm).

$^1$H NMR (CDCl$_3$) 7.35(NH9,d,9.9), 5.78(H10,t,9.8), 5.13(10—OCH$_2$, d,7.0), 4.82(10—OCH$_2$, D,6.9), 4.81(4=CH$_2$,t,1.9), 4.71(4=CH$_2$,t,2.0), 4.26(H7,s), 4.20(12,dd,6.5,10.3), 3.90(H2,dq,2.7,6.6), 3.79(H11,dd,6.6,9.6), 3.66(H18,dd,2.5,11.5), 3.55(13—OCH$_3$,s), 3.50(H18,dd,4.1,11.5), 3.43(H13,d,10.3), 3.28(H15,m), 3.27(6—,&17—OCH$_3$,s), 3.18(H17,m), 2.50(H5(eq),d,14.5), 2.34(H5(ax),td,2.0,14.5), 2.20(H3,dq,2.6,7.2), 1.74(H16,ddd,1.8,9.9,14.0), 1.52(H16,m) 1.18(2—CH$_3$,d,6.6), 1.00(3—CH$_3$,d.7.1), 0.98(14—CH$_3$(eq),s), 0.87(14—CH$_3$(ax),s), 0.20(7—OSi(CH$_3$)$_3$,s), 0.12(18—OSi(CH$_3$)$_3$,s), ppm(couplings in Hz).

$^1$H NMR (CD$_2$Cl$_2$) 7.37(NH9,d,10.2), 5.75(H10,t,9.8), 5.15(10—OCH$_2$,d,7.0), 4.82(10—OCH$_2$,d,7.0), 4.82(4=CH$_2$,t,2.0), 4.68(4=CH$_2$,t,2.1), 4.24(H7,s), 4.17(H12,dd,6.5,10.1), 3.87(H2,dq,2.7,6.6), 3.80(H11,dd,6.5,9.5), 3.65(H18,dd,2.5,11.5), 3.54(13—OCH$_3$,s), 3.49(H18,dd,4.3,11.5), 3.46(H13,d,10.1), 3.28(H15,m), 3.27 & 3.25(6—&17—OCH₃,s), 3.18(H17,m), 2.48(H5(eq),d,14.3), 2.34(H5(ax),td,2.1,14.5), 2.22(H3,dq,2.7,7.3), 1.69(H16,ddd,2.1,9.7,14.0) 1.51(H16,m), 1.19(2—CH₃,d,6.6), 1.01(3—CH₃,d.7.1), 1.00(14—CH₃(eq),s), 0.87(14—CH₃(ax),s), 0.22(7—OSi(CH₃)₃,s), 0.13(18—OSi(CH₃)₃,s), ppm(couplings in Hz).

¹³C NMR (CD₂Cl₂) 170.90(C8), 147.32(C4), 109.60(4=CH₂), 99.60(C6), 86.64(10—OCH₂), 79.72(C13), 78.94(C17), 77.38(C7), 76.02(C15), 74.54(C12), 73.34(C10), 70.71(C11,broad), 69.69(C2), 62.20(C18), 61.64(13—O—CH₃), 56.60(17—O—CH₃), 49.83(6—O—CH₃), 41.58(C3,C14), 35.76(C5), 29.59(C16), 23.31(14—CH₃(eq)), 17.85(2—CH₃), 13.70(14—CH₃(ax)), 11.90(3—CH₃), 0.28(7—OSi(CH₃)₃), −0.53(18—O(CH₃)₃).

AV assay: 4+, 4+, +*, @ 2 ng/disk; +, +, + @ 0.5 ng/disk

P388 IC₅₀: 0.19 ng/ml.

EXAMPLE 19

4α-Dihydro mycalamide A

The compound of the formula:

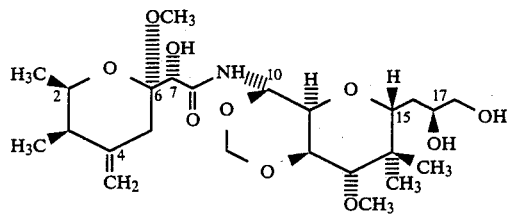

Mycalamide A (5.5 mg), in methanol solution, was stirred with Adam's catalyst (PtO₂,3mg) under H₂ for 1 hour, filtered and the solvent removed (5.4 mg). RPLC confirmed reduction and showed a 2:1 mix of the epimers at C4. These were separated by prep RPLC giving two fractions (1.3 mg, 2.6 mg), the major one being found to be a complex mixture, but the minor one being found to be a complex mixture, but the minor one to be the pure 4α- epimer of dihydro mycalamide A by PMR, being an oil having a molecular weight of 505 and a molecular formula C₂₄H₄₃NO₁₀.

Spectral data:
¹H NMR (CDCl₃) 7.46(NH9,d,10.2), 5.85(H10,t,9.6), 5.13(10—OCH₂,d,6.9), 4.87(10—OCH₂,d,6.9), 4.24(H7,s), 4.22(H12,dd,6.8,10.3), 3.97(H2,dq,2.6,6.6), 3.83(H11,dd,6.4,9.7), 3.75(H17,m), 3.6(H15,m,hidden), 3.56(13—OCH₃,s), 3.55(H18,m,hidden), 3.45(H13,d,10.2), 3.38(H18,dd,6.2,11.1), 3.30(6—OCH₃,s), 2.15(H4,m), 1.65(H5(ax),m), 1.4(H3,m), 1.4(H3,m), 1.18(2—CH₃,d,6.6), 0.98(14—CH₃(eq),s), 0.88(4—CH₃,d,6.9), 0.88(14—CH₃(ax),s), 0.73(3—CH₃,d,7.0) ppm(couplings in Hz). NB. H5(eq), H3, H₂16 not observed.

AV assay: 4+, 4+, +*, @ 20 ng/disk; −, +, +* @ 5 ng/disk,

P388 IC₅₀: 2.3 ng/ml.

EXAMPLE 20

Dihydro pseudomycalamide A

The compound of the formula:

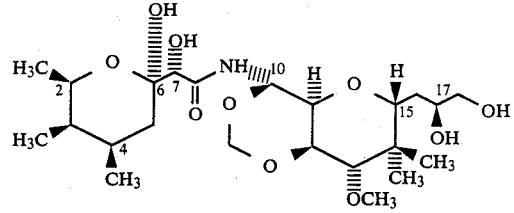

4α-dihydromycalamide A in CDCl₃ solution was rapidly hydrolyxed on the addition of D₂O to give 4α-dihydro pseudomycalamide A cleanly, which is an oil having a molecular weight of 491 and a molecular formula C₂₃H₄₁NO₁₀.

Spectral data:
DCIMS (NH₃) 509(9%,M+NH₄), 492(36%), 491(83%,M+NH₄30—H₂O), 474(16%, MH+—H₂O), 292(17%), 262(23%).

¹H NMR (CDCl₃) 7.49(NH9,d,9.9), 5.83(H10,t,9.9), 5.15(10—OCH₂,d,7.0), 4.89(10—OCH₂,d,7.0), 4.24(H12,dd,6.8,10.5), 4.20(H2,dq,2.4,6.6), 3.99(H7,s), 3.91(H11,dd,6.9,10.4), 3.74(H17,m), 3.59(H15,m,hidden), 3.56(13—OCH₃,s), 3.55(H18,m,hidden), 3.48(H13,d,10.5), 3.40(H18,dd,5.6,11.3), 2.2(H4,m), 1.67(H5(ax),t,13.2), 1.55(H₂16,m), 1.42(H5(eq),dd,4.1,13.5), 1.4(H3,m), 1.06(2—CH₃,d,6.6), 0.97(14—CH₃(eq),s), 0.90(4—CH₃,d,6.9), 0.87(14 —CH₃(ax),s), 0.72(3—CH₃,d,7.0) ppm(couplings in Hz).

C NMR (CD₂Cl₂) 97.09(C6), 87.04(10—OCH₂), 79.50(C13), 78.89(C15), 74.51(C12), 73.20(C10), 73.11(C7), 72.06(C17), 71.24(C11), 69.83(C2), 66.35(C18), 61.94(13—O—CH₃), 37.00(C3), 32.68(C5), 31.54(C16), 29.00(C4), 22.94(14—CH₃(eq)), 19.21(4—CH₃), 18.48(2—CH₃), 13.22(14—CH₃(ax)), 4.04(3—CH₃).

NB. C8, C14 not observed.

AV assay: 4+, 4+, +*, @ 200 ng/disk; 2+, +, +*, @ 50 ng/disk

P388 IC₅₀: 10.5 ng/ml.

EXAMPLE 21

6-trideuteromethoxy mycalamide A

The compound of the formula:

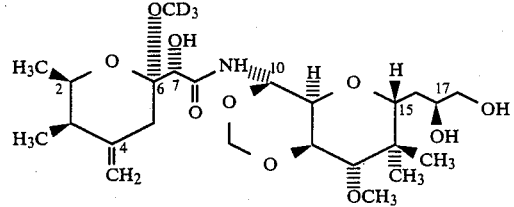

Mycalamide A (1.1 mg) was dissolved in CD₃OD containing about 0.1% trifluoroacetic acid and allowed to react at room temperature overnight. PMR confirmed complete exchange to give pure C6—OCD₃ mycalamide A, an oil having a molecular weight of 506 and a molecular formula C₂₄H₃₈D₃NO₁₀.

Spectral data:
DCIMS (NH₃) 524(16%,M+NH₄), 491(14%), 490(22%), 489(81%,M+NH₄+—CD₃OH), 472(16%,MH+—CD₃OH), 278(16%), 245(19%), 244(96%).

EXAMPLE 22

4β-dihydro mycalamide A

The compound of the formula:

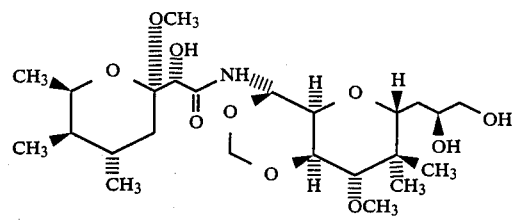

Mycalamide A (5.0 mg), in methanol solution, was stirred with Adam's catalyst (PtO₂, 3 mg) under H₂ for 1 hour, filtered and the solvent removed (5.4 mg). RPLC confirmed reduction and showed a 2:1 mix of epimers at C4. These were separated by prep RPL giving two fractions (1.5 mg, 2.6 mg), the major one being found to be the 4β-epimer of dihydro mycalamide A by PMR, which is an oil with molecular weight 505 and molecular formula $C_{24}H_{43}NO_{10}$.

AV assay: 3+, 3+, +*, @ 2 ng/disk, —, —, —, @ 0.5 ng/disk

P388 $IC_{50}$: 0.8 ng.ml.

EXAMPLE 23

4β-dihydro pseudomycalamide A

The compound of the formula:

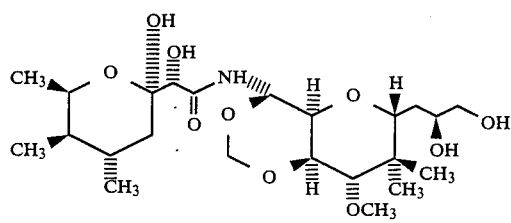

4β-dihydro mycalamide A dissolved in CD₂Cl₂ immediately hydrolysed yielding 4β-dihydro pseudomycalamide cleanly, an oil with molecular weight 491 and molecular formula $C_{23}H_{41}NO_{10}$.

Spectral data:
¹H NMR (CD₂Cl₂) 7.25(NH9,d,10.0), 5.84(H10,t,10.0), 5.17(10—OCH₂,d,7.0), 4.87(10—OCH₂,d,7.1), 4.44(H7,s), 4.22(H12,dd,6.9,10.6), 4.08(H2,dq,3.0,6.5), 3.88(H11,dd,6.9,10.0), 3.71(H17,m), 3.56(13—OCH₃,s), 3.55(H15,m,hidden), 3.53(H18,m), 3.52(H13,d,10.4), 3.35(H18,dd,6.5,11.3), 1.9(H4,m), 1.55(H₂16,m), 1.47(H3,m), 1.19(2—CH₃,d,6.6), 1.04(4—CH₃,d,7.0), 0.98(14—CH₃(eq),s), 0.88(4—CH₃,d,7.0), 0.87(14—CH₃(ax),s), ppm(couplings in Hz).

NB: H₂5 not observed.

AV assay: 4+, 4+, +*, @ 20 ng/disk, 2+, 2+, +*, @ 5 ng/disk.

P388 $IC_{50}$ 4.2 ng/ml

EXAMPLE 24

4β-Dihydro mycalamide B

The compound of the formula:

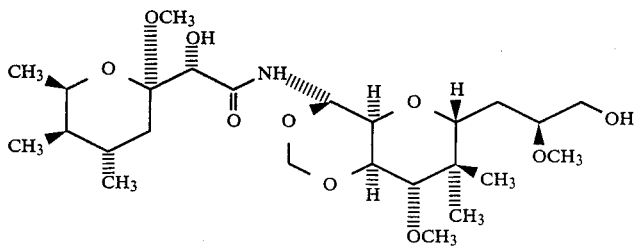

Mycalamide B (5.5 mg ca), in methanol solution, was stirred with Adam's catalyst (PtO₂,3 mg) under H₂ for 1 hour, filtered and the solvent removed (5.5 mg). RPLC confirmed reduction and showed a 3:2 mix of the epimers at C4. These were separated by prep RPLC giving two fractions (1.7 mg, 2.7 mg), the major one being found to be the 4β-epimer of dihydro mycalamide B and the minor one to be the 4α-epimer of dihydro mycalamide B, both 90% pure by PMR. the 4β-epimer is an oil having a molecular weight of 519 and a molecular formula $C_{25}H_{45}NO_{10}$.

Spectral data: ¹H NMR (CD₂Cl₂) 7.50(NH9,d,9.4), 5.76(H10,t,9.5), 5.13(10—OCH₂,d,7.0), 4.84(10—OCH₂,d,7.0), 4.18(H7,s), 4.18(H12,dd,6.5,10.2), 4.14(H2,dq,2.8,6.6), 3.83(H11,dd,6.7,9.5), 3.60(H18,dd,3.4,11.8), 3.54(13—OCH₃,s), 3.45(H13,d,10.3), 3.42(H18,dd,6.2,11.9), 3.41(H15,dd,2.4,9.5,partly hidden), 3.28(17—OCH₃,s), 3.27(6—OCH₃,s), 3.24(H17,m), 1.69(H4,m), 1.64(H5(ax),m), 1.5-1.6(H₂16,m), 1.53(H5(eq),m), 1.37(H3,m), 1.19(2—CH₃,d,6.6), 1.18(4—CH₃,d,7.3), 1.00(14—CH₃(eq),s), 0.96(3—CH₃,d,7.1), 0.87(14—CH₃(ax),s), ppm(couplings in Hz).

¹³C NMR (CD₂Cl₂) 171.97(C8), 100.30(C6), 86.72(10—OCH₂), 79.63(C13), 79.23(C17), 75.60(C15), 74.58(C12), 74.15(C10), 73.04(C7), 70.92(C11), 64.90(C2), 63.78(C18). 61.68(13—O—CH₃), 56.65(C17—OCH₃), 47.90(6—OCH₃), 37.56(C3), 32.44(C5), 29.67(C16), 29.50(C4), 23.20(14—CH₃(eq)), 20.80(4—CH₃), 1828(2—CH₃). 13.03(3—CH₃). NB. C14, 14—CH₃(ax) not observed.

AV assay: 4+, 4+, +*, @ 2 ng/disk; +, 2+, +*, @ 0.5 ng/disk

P388 $IC_{50}$: 0.14 ng/ml.

EXAMPLE 25

4α-Dihydro mycalamide B

The compound of the formula:

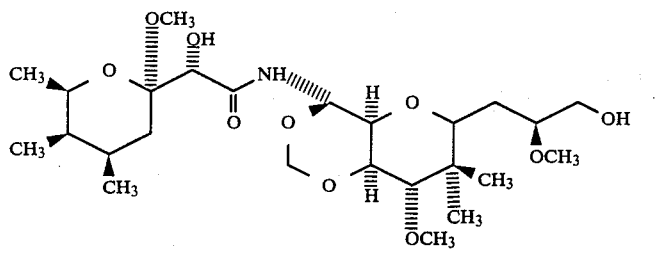

The 4α-epimer of dihydro mycalamide B, prepared in the manner described in Example 24, is an oil having a molecular weight of 519 and a molecular formula $C_{25}H_{45}NO_{10}$.

Spectral data:
$^1$H NMR (CD$_2$Cl$_2$) 7.53(NH9,d,9.3), 5.74(H10,t,9.4), 5.12(10—OCH$_2$,d,7.0), 4.84(10—OCH$_2$,d,6.9), 4.21(H7,s), 4.16(H12,dd,6.1,9.6), 3.99(H2,dq,2.4,6.6), 3.81(H11,dd,6.5,9.3), 3.64(H18,m), 3.54(13—OCH$_3$,s), 3.45(H18,m), 3.44(H13,d,10.0), 3.42(H15,m,hidden), 3.30(17—OCH$_3$,s), 3.29(6—OCH$_3$,s), 3.25(H17,m), 2.18(H4,m), 1.5-1.6(H$_2$16,m), 1.20(2—CH$_3$,d,6.6), 1.01(14—CH$_3$(eq),s), 0.89(4—CH$_3$,d,6.3), 0.88(14—CH$_3$(ax),s), 0.76(3—CH$_3$,d,7.1) ppm(couplings in Hz). NB: H$_2$5, H3 not observed.

EXAMPLE 26

4αDihydro pseudomycalamide B

The compound of the formula:

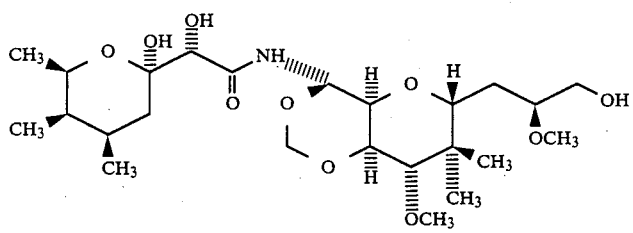

4α-dihydro mycalamide B in CD$_2$Cl$_2$ solution hydrolysed overnight to give 4α-dihydro pseudo-mycalamide B which is an oil having a molecular weight of 505 and a molecular formula $C_{24}H_{43}NO_{10}$.

Spectral data:
$^1$H NMR (CD$_2$Cl$_2$) 7.54(NH9,d,9.3), 5.67(H10,t,9.5), 5.16(10—OCH$_2$,d,7.0), 4.99(6—OH,d,2.2), 4.85(10—OCH$_2$,d,7.0), 4.21(H12,dd,7.1,10.0), 4.20(H2,dq,2.6,6.5), 3.95(H7,d,6.9), 3.92(H11,dd,6.7,10.1), 3.82(7—OH,d,6.8), 3.55(13—OCH$_3$,s), 3.54(H18,m,hidden), 3.47(H13,d,9.8), 3.44(H18,m,hidden), 3.37(H15,m), 3.31(17—OCH$_3$,s), 3.3(H17,m), 2.23(H4,m), 1.69(H59(ax),dt,2.0,13.2), 1.55(H$_2$16,m), 1.45(H3,m), 1.37(H59(eq),dd,3.9,13.2), 1.07(2—CH$_3$,d,6.6), 0.98(14—CH$_3$(eq),s), 0.92(4—CH$_3$,d,7.0), 0.87(14—CH$_3$(ax),s), 0.73(3—CH$_3$,d,7.1) ppm(couplings in Hz).

$^{13}$C NMR (CD$_2$Cl$_2$) 86.89(10—OCH$_2$), 79.30(C13), 79.04(C17), 75.28(C15), 74.73(C12), 74.62(C10), 73.40(C7), 70.65(C11), 69.90(C2), 63.92(C18), 61.84(13—O—CH$_3$), 56.79(C17—OCH$_3$), 41.84(C14), 32.27(C3), 32.84(C5), 29.22(C16), 28.85(C4), 22.84(14—CH$_3$(eq)), 19.20(4—CH$_3$), 18.45(2—CH$_3$), 13.08(14—CH$_3$(ax)), 3.95(3—CH$_3$). NB: C8, C6 not observed.

AV assay: 4+, 4+, +*, @ 20 ng/disk; —, —, —, @ 5 ng/disk
P388 IC$_{50}$: 3 ng/ml.

EXAMPLE 27

Pseudomycalamide B

The compound of the formula:

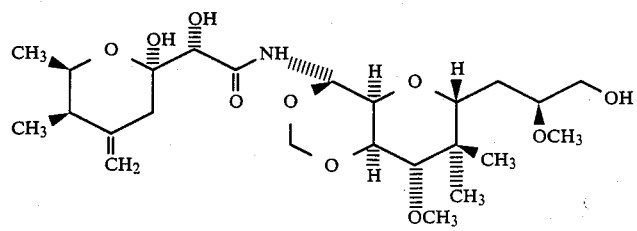

Mycalamide B (5.5 mg) was dissolved in CH$_2$Cl$_2$ (0.5 ml) and stirred with a 1% aqueous solution of p-toluene sulfonic acid (0.2 ml) for 48 hours at room temperature. The organic extract was washed with water (3×0.3 ml), extracted in CH$_2$Cl$_2$ and the solvent removed to give 5.1 mg of 85% pure pseudomycalamide B, containing a small amount of mycalamide B by PMR. This compound is an oil having a molecular weight of 503 and a molecular formula $C_{24}H_{41}NO_{10}$.

Spectral data:
$^1$H NMR (CD$_2$Cl$_2$) 7.64(NH9,d,9.6), 5.68(H10,t,9.6), 5.17(10—OCH$_2$,d,7.0), 4.88(4=CH$_2$,t,2.0), 4.86(10—OCH$_2$,d,7.1), 4.74(4=CH$_2$,t,2.1), 4.22(H12,dd,6.7,10.5), 4.18(H2,dq,2.7,6.6), 4.02(H7,s), 3.94(H11,dd,6.8,10.1), 3.56(13—OCH$_3$,s), 3.52(H13,d,10.5), 3.47(H18,m), 3.4*(H18,m), 3.38*(H17,m), 3.33*(H15,m), 3.31(17—OCH$_3$,s), 2.82(H5(ax),dt,2.2,13.8), 2.22(H3,dq,2.7,7.0), 2.12(H5(eq),d,13.7), 1.5–1.65(H₂16,m), 1.09(2—CH₃,d,6.5), 1.01(3—CH₃,d,7.1), 0.98(14—CH₃(eq),s), 0.87(14—CH₃(ax),s) ppm(couplings in Hz). NB: * exact positions uncertain.

$^{13}$C NMR (CD₂Cl₂) 174.44(C8), 147.33(C4), 109.79(4=CH₂), 97/76(C6), 86.88(10—OCH₂), 79.26(C13), 78.95(C17), 75.04(C15), 74.71(C7*), 74.54(C12*), 73.44(C10*), 70.61(C11), 68.95(C2), 63.97(C18), 61.84(13—O—CH₃), 56.78(C17—OCH₃), 41.85(C14), 41.67(C3), 35.59(C5), 28.82(C16), 22.84(14—CH₃(eq)), 17.83(2—CH₃), 13.07(14—CH₃(ax)), 11.77(3—CH₃). NB: * assignments uncertain.

AV assay: 4+, 4+, +*, @ 5 ng/disk; —, —, —, @ 2 ng/disk

P388 IC₅₀: 1.8 ng/ml.

EXAMPLE 28

Pseudomycalamide A

The compound of the formula:

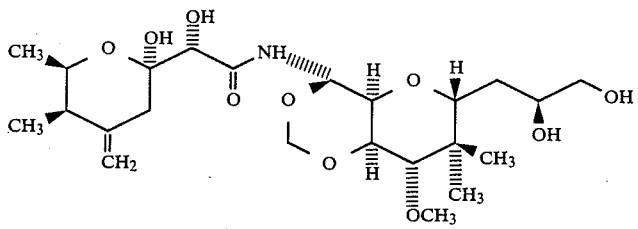

Mycalamide A (2.5 mg) was dissolved in CH₂Cl₂ (0.5 ml) and stirred with a 1% aqueous solution of p-toluene sulfonic acid (0.2 ml) for 6 hours at room temperature. The organic extract was washed with water (3×0.3 ml), extracted in CH₂Cl₂ and the solvent removed to give 2.1 mg of pure pseudomycalamide A which is an oil having a molecular weight of 489 and a molecular formula $C_{23}H_{39}NO_{10}$.

Spectral data:

$^1$H NMR (CD₂Cl₂) 7.61(NH9,d,9.8), 5.83(H10,t,10.0), 5.18(10—OCH₂,d,7.1), 4.88(10—OCH₂,d,7.0), 4.88(4=CH₂,t,2.0), 4.75(4=CH₂,t,2.2), 4.24(H12,dd,6.8,10.5), 4.18(H2,dq,2.7,6.6), 4.05(H7,broad d,6.1), 3.96(H11,dd,6.8,10.2), 3.73(H17,m), 3.58(H18,m,hidden), 3.56(13—OCH₃,s), 3.53(H13,d,10.5), 3.40(H18,dd,6.2,11.2), 2.82(H5(ax),td,2.0,13.8), 2.23(H3,dq,2.7,7.1), 2.14(H5(eq),d,13.8), 1.5–1.6(H₂16,m), 1.09(2—CH₃,d,6.6), 1.01(3—CH₃,d,7.0), 0.99(14—CH₃(eq),s), 0.88(14—CH₃(ax),s) ppm(couplings in Hz). NB: H15 not observed.

$^{13}$C NMR (CD₂Cl₂) 168.82(C8), 147.14(C4), 109.94(4=CH₂), 97.93(C6), 87.21(10—OCH₂), 79.56(C13), 79.01(C15), 74.96(C12*), 74.74(C7*), 73.42(C10*), 72.50(C11), 71.31(C7), 69.02(C2), 66.61(C18), 61.88(13—O—CH₃), 42.00(C14), 41.65(C3), 35.80(C5), 31.72(C16), 22.79(14—CH₃(eq)), 17.84(2—CH₃), 13.19(14—CH₃(ax)), 11.74(3—CH₃). NB: * assignments uncertain.

AV assay: 4+, 4+, +*, @ 200 ng/disk; 3+, 3+, +*, @ 50 ng/disk

P388 IC₅₀: 23 ng/ml.

Biological Activity Assays

Antitumor

Antitumor effectiveness of the compounds of the invention was evaluated using a standardized in vitro P388 mouse leukemia cell assay protocol disclosed in U.S. Pat. No. 4,731,366 with the antitumor activity being expressed in IC₅₀ (concentration that results in 50% inhibition of cell replication normalized to untreated cultures) determined with a log-log transform of data and expressed as xx ng/ml. As an example, for mycalamide A the P388 assay value was IC₅₀=1.6 ng/ml.

Antitumor effectiveness of mycalamide A was also evaluated using a standardized in vivo procedure by injecting mice with the test material starting 24 hours after P338 tumor implantation. A T/C value is calculated using the formula % T/C=Median survival of test group/Median survival of control group×100%, A T/C value above 130% is considered significant. This resulted in the following test data:

| | Median T/C % | |
|---|---|---|
| Dose mg/kg | 1st series | 2nd series |
| 0.02 | Toxic | 106 |
| 0.01 | 116 | 156 |
| 0.005 | 132 | 133 |
| 0.0025 | 137 | 122 |
| 0.0012 | | 117 |

In vivo antitumor activity of mycalamide A was also tested with an B16 murine melanoma assay resulting in the following data:

| Dose mg/kg | Median T/C % | Cures |
|---|---|---|
| 0.5 | Toxic | 0 |
| 0.25 | 214 | 1 |
| 0.125 | 189 | 0 |
| 0.0625 | 197 | 0 |

It is apparent from the in vitro and in vivo data reported above, that mycalamide A is effective for inhibiting or destroying tumors and therefore in controlling diseases caused by or related to such tumors in hosts, including mammals, such as cancerous cachexia.

Antiviral

Anitviral effectiveness of mycalamide A against both Herpes simplex type 1 virus (HVS—1) and *Vesicular stomatitis* virus (VSV) replicated in the CV—1 cell line. CV—1 is a fibroblast-like cell culture derived from primary African green monkey cells. A59 coronavirus tests were also conducted in vitro.

Antiviral activity is scored from 0 to +++, where +++=complete inhibition of plaque formation, ++=partial inhibition,+=less partial inhibition and and 0=no protection.

Cytotoxicity was determined in 24 well tissue culture plates of 16 mm diameter. Discs are 6 mm in diameter. Zones of cytotoxicity greater than 6 mm are graded from 8 to 16 using only even numbers, in which, 0=no macroscopic or microscope cytotoxicity, 16=100% or complete cell distruction, 8, 19, 12, 14=partial cytotoxicity, i.e., diameter of toxic zone including diameter of 6 mm. disc.

This antiviral assay work produced the following data for mycalamide A:

| Dose (ug/well) | VSV Cyt | VSV AV | HSV-1 Cyt | HSV-1 AV | A-59 Cyt | A-59 AV |
|---|---|---|---|---|---|---|
| 40 | 16 | | 16 | | 50 | 3+ |
| 20 | 16 | | 16 | | 50 | 3+ |
| 2 | 16 | | | | 50 | 3+ |
| 0.2 | 12 | 2+ | 12 | 2+ | 0 | 2+/3+ |

Mycalamide A was also tested in vivo with an A59 procedure in which four week old mice are inoculated intraperitoneally with 42 LD$_{50}$ doses of virus. Mycalamide A is administered on the same day and for 9 consecutive days thereafter. Mice are held for observation for 14 days total. Mice inoculated with virus only are expected to die in 3 to 7 days with a mortality rate of 80 to 100%. A reading of 0% mortality in mice receiving drug plus virus indicates protection from gross clinical disease and death. The results of this protocol are reported in the following table:

| Mice | Drug conc. (mg/kg) | | Cumulative Mortality Group Days after Infection | | | | | | |
|---|---|---|---|---|---|---|---|---|---|
| | | | 2 | 4 | 6 | 8 | 10 | 12 | 14 |
| Drug | 4 | 1 | 0 | 0 | 100 | 100 | 100 | 100 | 100 |
| Drug + virus | 4 | 1 | 0 | 0 | 75 | 100 | 100 | 100 | 100 |
| Drug | 4 | 0.1 | 0 | 0 | 0 | 0 | 0 | 0 | 0 |
| Drug + virus | 4 | 0.1 | 0 | 0 | 0 | 0 | 0 | 0 | 0 |
| Drug | 4 | 0.01 | 0 | 0 | 0 | 0 | 0 | 0 | 0 |
| Drug + virus | 4 | 0.01 | 0 | 0 | 25 | 25 | 25 | 25 | 25 |
| Virus only | 8 | | | 0 | 63 | 88 | 100 | 100 | 100 |
| Ribavirin (control) + virus | 4 | 100 | 0 | 0 | 0 | 0 | 0 | 0 | 0 |

The compounds of Examples 2-28 were subjected to antiviral assay evaluation similar to that reported above using polio vaccine virus Type I (PVI) in place of VSV and using BSC cells rather than CV—1. In this protocol, bioassay discs (6.0 mm Schleicher and Schuell) are soaked with the desired amount of test solution, then air dried at ambient temperature for 20 min. The discs are then pushed through the overlay to sit directly on the monolayer contained in a 16 mm diameter well and incubated in 5% CO$_2$ enriched atmosphere at 37 C for 24 hr. Wells are examined, using an inverted microscope, for the size of antiviral and/or cytotoxic zones to evaluate the wells for the antiviral and cytotoxicity results according to the scale: − =no discernable antiviral or cytotoxic effects, + =antiviral or cytotoxic zone 1-2 mm excess radius from disc, 2+ =zone of excess radius 2-4 mm, 3+ =zone of excess radius above 4 mm, 4+ =effect over the whole well.

In reporting these values in Examples 2-28, the first value is for HSV, the second for PVI and the third for cytotoxicity (where +* implies diffuse cytotoxicity over the whole well). Thus, 4+, 4+, −, 5 ng/disk means 4+ for HSV, 4+ for PVI, negative for cytotoxicity with the drug at 5 ng/disk.

DISCUSSION OF VARIABLES

Therapeutic and prophylactic application of the new compounds and compositions containing them can be contemplated to be accomplished by any suitable method and technique presently or prospectively known to those skilled in the art. Further, the compounds of the invention have use as starting materials or intermediates for the preparation of other useful compounds and compositions.

The administration of the mycalamide compounds of the invention is useful for treating antitumor and antiviral infections. Thus, pharmaceutical compositions containing compounds of the invention as active ingredients are useful in prophylactic or therapeutic treatment of humans or other mammals infected with or likely to be infected with tumors and virus.

The dosage administered will be dependent upon the identity of the tumor or virus infection, the type of host involved, its age, health, weight, kind of concurrent treatment, if any, frequency of treatment, therapeutic ratio and like considerations. Advantageously, dosage levels of the administered active ingredients can be, for examples, dermal, 1 to about 500 mg/kg; orally, 0.01 to 200 mg/kg; intranasal 0.01 to about 100 mg/kg and aerosol 0.01 to about 50 mg/kg of animal body weight.

Expressed in terms of concentration, the active ingredient of the invention can be present in the new compositions for localized use dermally, intranasally, bronchially, intramuscularly, intravaginally, intravenously, or orally in a concentration of from about 0.01 to about 50% w/w of the composition, and especially from about 0.1 to about 30% w/w of the composition.

The compositions of the invention are advantageously used in a variety of forms, e.g., tablets, ointments, capsules, pills, powders, aerosols, granules and oral solutions or suspensions and the like containing the indicated suitable quantities of the active ingredient. Such compositions are referred to herein and in the accompanying claims generically as "pharmaceutical compositions". Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils and such mixtures can be emulsified if desired.

In accordance with the invention, pharmaceutical compositions comprise, as an active ingredient, an effective amount of one or more of the new compounds and one or more non-toxic, pharmaceutically acceptable ingredient. Examples of such ingredients for use in the compositions include, ethanol, dimethyl sulfoxide, glycerol, silica, alumina, starch, calcium carbonate, talc, flour, and equivalent non-toxic carriers and diluents.

In preferred embodiments for production of the new compounds by extraction from marine sponges, etc., suitable organic solvent systems for extraction can be selected from methanol, ethyl acetate, acetone, diethyl ether, t-butyl methyl ether, ethanol, and isopropanol. Mixtures of two or more of such solvents in various ratios and combinations are advantageous.

Compounds of the invention are synthesized and/or isolated by various fractionation and chromatographic techniques from the extracts obtained as disclosed. Preferred isolation procedures include various chromatography techniques, e.g., countercurrent chromatography with suitable columns, including multi-layer planetary coil columns. A variety of solvents are available for use as single or mixed eluents, such as tetrahydrofuran, methanol, ethyl acetate, acetonitrile, n-propanol, n-butanol, water, and equivalent solvents. Further purifications using such procedures may also be carried out on the recovered extractions. Preferred isolation techniques for further purificaation include chromatographic operations such as high-pressure, liquid chromatography with suitable columns and suitable solvents.

The embodiments of the invention in which an exclusive property or privilege is claimed are defined as follows:

1. A compound selected from the formula:

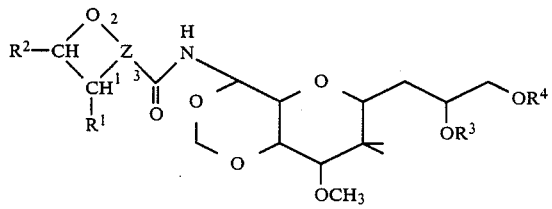

wherein Z is

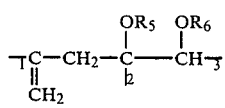

-continued

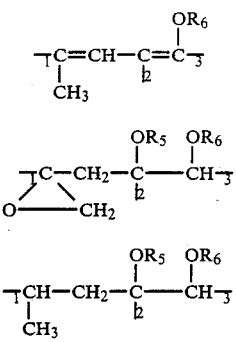

$R^1$ and $R^2$ are methyl and $R^{3-6}$ are the same or different and are hydrogen, lower alkyl, carboxylic acyl or lower tri-(lower alkyl) silyl.

2. The compound of claim 1 of the formula:

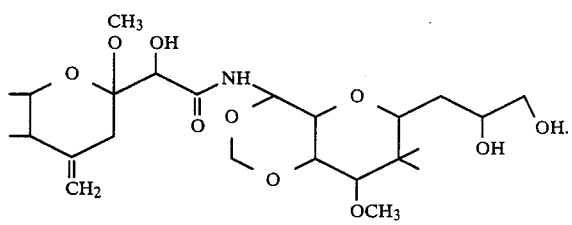

3. The compound of claim 1 of the formula:

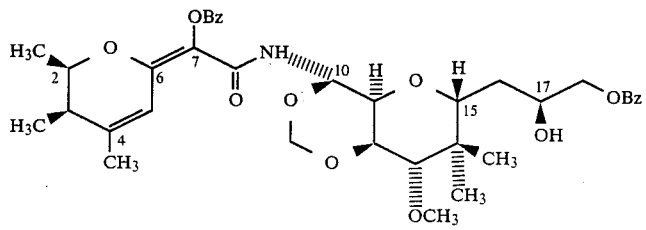

wherein Bz is bromobenzoyl.

4. A pharmaceutical composition comprising between about 0.01 to 50% by weight based on the total weight of said composition as an active ingredient one or more compounds of claim 1 and a non-toxic carrier or diluent.

5. A pharmaceutical composition comprising between about 0.1 to 25% by weight based on the total weight of said composition as an active ingredient the compound of claim 3 and a non-toxic carrier or diluent.

6. A compound of the formula:

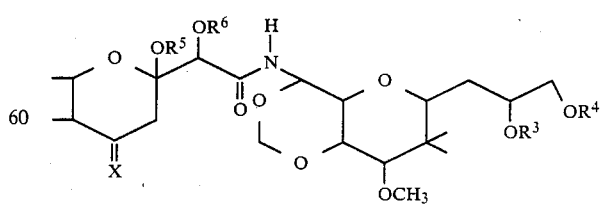

wherein $R^{3-6}$ are the same or different and are hydrogen, lower alkyl, carboxylic acyl or tri-(lower alkyl) silyl, and X is $=CH_2$,

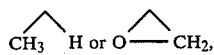
7. A compound of the formula:
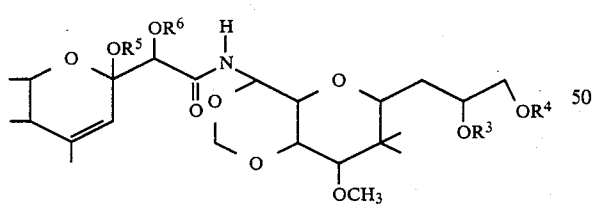
wherein $R^{3-6}$ are the same or different and are hydrogen, lower alkyl, carboxylic acyl or tri-(lower alkyl) silyl.
8. A compound according to claim 6 of the formula:
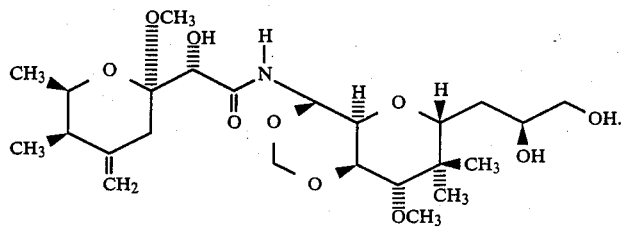
9. A compound according to claim 6 of the formula:
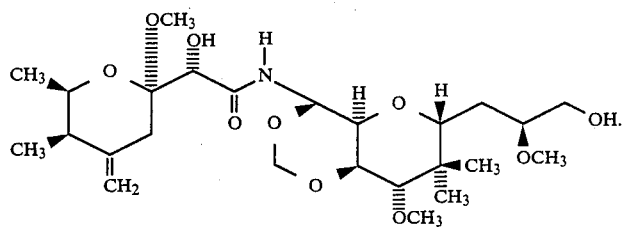
10. A compound according to claim 6 of the formula:
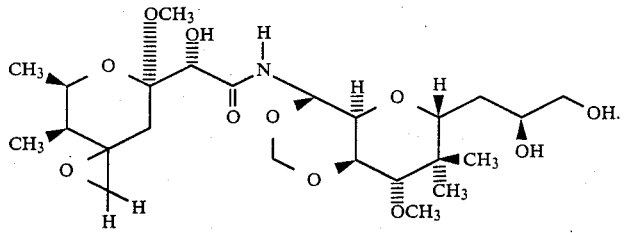
11. A compound according to claim 6 of the formula:
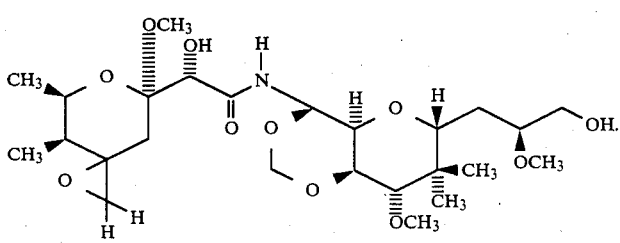
12. A compound according to claim 6 of the formula:

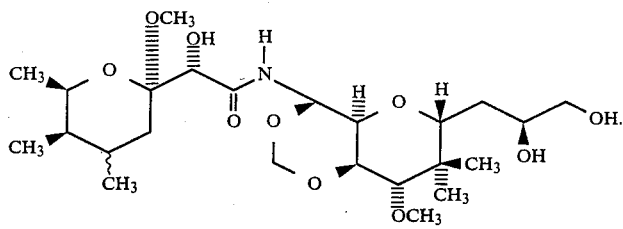

13. A compound according to claim 6 of the formula:

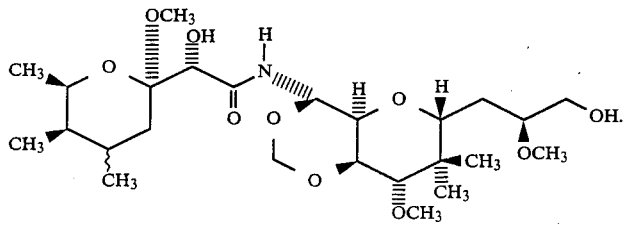

14. A pharmaceutical composition comprising between about 0.01 to 50% by weight based on the total weight of said composition as an active ingredient the compound of claim 5 and a non-toxic carrier or diluent.

15. A pharmaceutical composition comprising between about 0.01 to 50% by weight based on the total weight of said composition as an active ingredient one or more of the compounds of claim 11 and a non-toxic carrier or diluent.

16. A pharmaceutical composition comprising between about 0.01 to 50% by weight based on the total weight of said composition as an active ingredient one or more of the compounds of claim 7 and a non-toxic carrier or diluent.

17. A pharmaceutical composition comprising between about 0.01 to 50% by weight based on the total weight of said composition as an active ingredient the compound of claim 8 and a non-toxic carrier or diluent.

18. A pharmaceutical composition comprising between about 0.01 to 50% by weight based on the total weight of said composition as an active ingredient the compound of claim 9 and a non-toxic carrier or diluent.

19. A pharmaceutical composition comprising between about 0.01 to 50% by weight based on the total weight of said composition as an active ingredient the compound of claim 10 and a non-toxic carrier or diluent.

20. A pharmaceutical composition comprising between about 0.01 to 50% by weight based on the total weight of said composition as an active ingredient the compound of claim 11 and a non-toxic carrier or diluent.

21. A pharmaceutical composition comprising between about 0.01 to 50% by weight based on the total weight of said composition as an active ingredient the compound of claim 12 and a non-toxic carrier or diluent.

22. A pharmaceutical composition comprising between about 0.01 to 50% by weight based on the total weight of said composition as an active ingredient the compound of claim 13 and a non-toxic carrier or diluent.

* * * * *

UNITED STATES PATENT AND TRADEMARK OFFICE
CERTIFICATE OF CORRECTION

PATENT NO. : 4,868,204

DATED : September 19, 1989

INVENTOR(S) : John W. Blunt et al.

It is certified that error appears in the above-identified patent and that said Letters Patent is hereby corrected as shown below:

Column 1: line 55: "reservovirs" should read --reservoirs--.
Column 2: line 36: "description" should read --description.--.
Column 4: line 62: "50.27220" should read --503.27220--; line 67: "3700-3700" should read --3700-3100--.

Column 5:

Column 5:

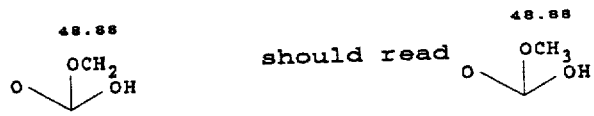

Column 5: line 61: was omitted, should read 512(19%), 511(34%), 510(100%), 509(82%), 508(29%).

UNITED STATES PATENT AND TRADEMARK OFFICE
CERTIFICATE OF CORRECTION

PATENT NO. : 4,868,204

DATED : September 19, 1989

INVENTOR(S) : John W. Blunt et al.

It is certified that error appears in the above-identified patent and that said Letters Patent is hereby corrected as shown below:

Column 6: line 49: "2.36(HS" should read --2.36(H5--; line 54: "C NMR" should read --$^{13}$C NMR--; line 66: "4 $\gamma$-epoxide" should read --4 $\alpha$-epoxide--.

Column 7: line 54: "2.22(HS(ax, d, 14.8)" should read --2.22(H5(ax), d, 14.8)--; line 55: "1.43(HS(eq)" should read --1.43(H5(eq)--; line 59: "C NMR" should read --$^{13}$C NMR--.

Column 8:

line 51: "(H7,2)" should read --(H7,s)--; line 53: "3.63(H14" should read --3.63(H15--; line 57: "2.10(HS" should read --2.10(H5--; line 58: "1.43(HS" should read --1.43(H5--; line 67: "(eq)" should read --(eq))--.

Column 9: line 55: "3.30(17-O-CH, s)" should read --3.30(17-O-CH$_3$, s)--; line 57: "2.13(HS" should read --2.13(H5--; line 58: "1.44(HS" should read --1.44(H5--.

Column 10: line 3: "B 4 $\delta$-epoxide" should read --B 4 $\beta$-epoxide--; line 46: "5.13(10-)CH$_2$" should read --5.13(10-OCH$_2$--.

UNITED STATES PATENT AND TRADEMARK OFFICE
CERTIFICATE OF CORRECTION

PATENT NO. : 4,868,204

DATED : September 19, 1989

INVENTOR(S) : John W. Blunt et al.

It is certified that error appears in the above-identified patent and that said Letters Patent is hereby corrected as shown below:

Column 11:

Column 11: line 49: "3.99(H2, dl" should read --3.99(H2, dq--; line 58: "18-O-C)" should read --18-O-CO)--.

Column 12: 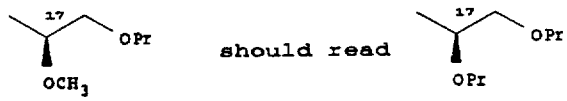

Column 12: line 46: "3.99(HZ, dl" should read --3.99(H2, dq--; line 48: "2.49. 2.37" should read --2.49, 2.37--; line 51: "(16,m)" should read --(H16, m)--; line 52: "1.0-1.21" should read --1.04-1.21--.

Column 13: line 47: "2.20(7-O.CO.C$_3$, s)" should read --2.20(7-O.CO.CH$_3$, s)--; line 48: "2.08(18-O.C.CH$_3$, s)" should read --2.08(18-O.CO.CH$_3$, s)--; line 52: "-C NMR" should read --$^{13}$C NMR--.

Column 15: line 60: "128.74" should read --128.73--.

Column 16: line 33: "5.97(HS" should read --5.97(H5--; line 64: "(30 x 0.2 ml)" should read --(3 x 0.2 ml)--.

UNITED STATES PATENT AND TRADEMARK OFFICE
CERTIFICATE OF CORRECTION

PATENT NO. : 4,868,204

DATED : September 19, 1989

INVENTOR(S) : John W. Blunt et al.

It is certified that error appears in the above-identified patent and that said Letters Patent is hereby corrected as shown below:

Column 17: line 65: "2.35(HS" should read --2.35(H5--.

Column 18: line 11: "2.54(HS" should read --2.54(H5--; line 11: "2.35(HS" should read --2.35(H5--; line 19: "(C11, braod)" should read --(C11, broad)--; line 21: "50.05(61-O" should read --50.05(6-O--; line 59: "(10-OCH$_2$, d, -b 7.0)" should read --(10-OCH$_2$, d, 7.0)--; line 61: "(4=CH$_2$m)" should read --(4=CH$_2$, m)--.

Column 19: line 38: "ethyl acetate," should read --ethyl acetate.--; line 53: "2.34(HS(eq)" should read --2.34(H5(eq)--; line 56: "(3-CH$_3$d.7.2)" should read --(3-CH$_3$, d.7.2)--; line 67: "3.20(16-OCH$_3$, s)" should read --3.20(17-OCH$_3$, s)--; line 68: "2.30(HS" should read --2.30(H5--.

Column 20: line 48: "(10-OCH$_2$, D, 6.9)" should read --(10-OCH$_2$, d, 6.9)--; line 51: "(12, dd, 6.5, 10.3)" should read --(H12, dd, 6.5, 10.3)--.

Column 21: line 18: "+, +, +" should read -- --, --, -- --.

Column 21:       should read   

UNITED STATES PATENT AND TRADEMARK OFFICE
CERTIFICATE OF CORRECTION

PATENT NO. : 4,868,204

DATED : September 19, 1989

INVENTOR(S) : John W. Blunt et al.

It is certified that error appears in the above-identified patent and that said Letters Patent is hereby corrected as shown below:

Column 21: lines 43-44: "but the minor one being found to be a complex mixture," should be deleted; line 57: "1.4(H3, m)" second one should be deleted.

Column 22: line 13: "hydrolyxed" should read --hydrolysed--; line 18: "(83%, $M+NH_430-H_2O$)" should read --(83%, $M+NH_4^+-H_2O$)--; line 32: "C NMR" should read --$^{13}C$ NMR--.

Column 23: line 35: "RPL" should read --RPLC--.

Column 24: line 37: "PMR. the" should read --PMR. The--; line 46: "3.45(H13" should read --3.46(H13--; line 59: "1828(2-" should read --18.28(2- --.

Column 27: line 7: "97/76(C6)" should read --97.76(C6)--.

Column 31: line 44: "purificaation" should read --purification--.

Signed and Sealed this

Ninth Day of October, 1990

Attest:

HARRY F. MANBECK, JR.

*Attesting Officer*  *Commissioner of Patents and Trademarks*